United States Patent [19]

Wrobel et al.

[11] Patent Number: 4,962,224

[45] Date of Patent: Oct. 9, 1990

[54] N-NAPHTHOYLGLYCINES AS ALDOSE REDUCTASE INHIBITORS

[75] Inventors: Jay E. Wrobel, Lawrenceville; John G. Bauman, E. Windsor; Kazimir Sestanj, Monmouth Junction, all of N.J.

[73] Assignee: American Home Products Corporation, New York, N.Y.

[21] Appl. No.: 397,623

[22] Filed: Aug. 22, 1989

Related U.S. Application Data

[63] Continuation of Ser. No. 137, 403, Dec. 23, 1987, abandoned.

[51] Int. Cl.$^5$ .......................................... C07C 261/00
[52] U.S. Cl. ........................................ 560/28; 560/10; 562/427; 562/444; 564/74
[58] Field of Search .................... 560/10, 28; 562/427, 562/444; 564/74, 158; 514/487, 534, 599, 616, 481, 510

[56] References Cited

U.S. PATENT DOCUMENTS

| | | | |
|---|---|---|---|
| 4,391,816 | 7/1983 | Sestanj | 424/274 |
| 4,391,825 | 7/1983 | Bellini | 560/39 |
| 4,439,617 | 3/1984 | Sestanj | 560/39 |
| 4,447,452 | 5/1984 | Sestanj | 424/319 |
| 4,568,693 | 2/1986 | Sestanj | 514/524 |
| 4,600,724 | 7/1986 | Sestanj | 562/427 |
| 4,672,058 | 6/1987 | Bellini | 514/62 |
| 4,672,059 | 6/1987 | Sestanj | 514/62 |
| 4,699,993 | 10/1987 | Brandt | 558/423 |
| 4,785,018 | 11/1988 | Murase | 560/10 |

*Primary Examiner*—Michael L. Shippen
*Attorney, Agent, or Firm*—Walter Patton

[57] ABSTRACT

Disclosed herein are N-naphthoylglycines and methods of their preparation. The N-naphthoylglycines are novel aldose reductase inhibitors useful for the treatment or prevention of diabetic complications.

2 Claims, No Drawings

N-NAPHTHOYLGLYCINES AS ALDOSE REDUCTASE INHIBITORS

This is a continuation application of copending U.S. application Ser. No. 07/137,403, filed Dec. 23, 1987, now abandoned.

BACKGROUND OF THE INVENTION

This invention relates to N-naphthoylglycines, to the processes for their preparation, to methods for using the compounds, and to pharmaceutical preparations thereof. The compounds have pharmaceutical properties which render them beneficial for the treatment of diabetes mellitus and associated conditions.

For many years diabetes mellitus has been treated with two established types of drugs, namely insulin and oral hypoglycemic agents. These drugs have benefited hundreds of thousands of diabetics by improving their well-being and prolonging their lives. However, the resulting longevity of diabetic patients has led to complications such as neuropathy, nephropathy, retinopathy, cataracts and atherosclerosis. These complications have been linked to the undesirable accumulation of sorbitol in diabetic tissue, which in turn resulted from the high levels of glucose characteristic of the diabetic patient.

In mammals, including humans, the key enzyme involved in the conversion of hexoses to polyols (e.g. the sorbitol pathway) is aldose reductase. J. H. Kinoshita and collaborators, see J. H. Kinoshita et al, Biochem. Biophys. Acta, 158,472 (1968) and references cited therein, have demonstrated that aldose reductase plays a central role in the etiology of galcatosemic cataracts by effecting the conversion of galactose to dulcitol (galactitol) and that an agent capable of inhibiting aldose reductase can prevent the detrimental accumulation of dulcitol in the lens. Furthermore, a relationship between elevated levels of glucose and an undesireable accumulation of sorbitol has been demonstrated in the lens, peripheral nervous cord and kidney of diabetic animals, see A. Pirie and R. van Heyningen, Exp. Eye Res., 3,124 (1964); L. T. Chylack and J. H. Kinoshita, Invest. Ophthal., 8,401 (1969) and J. D. Ward and R. W. R. Baker, Diabetol., 6,531 (1970).

The closest prior art is K. Sestanj et al, U.S. Pat. No. 4,568,693, 1986, (Example 52) and U.S. Pat. No. 4,439,617, 1984, (Example 60). K. Sestanj et al, disclose N-naphthoylglycine derivatives having aldose reductase activity. The compounds of the present invention differ in that they contain a 2-substituent on the naphthalene ring. Still other related compounds having a similar utility are N-naphthoylglycine derivatives of Bellini et al, U.S. Pat. No. 4,672,058, 1987, and K. Sestanj et al, U.S. Pat. No. 4,672,059, 1987; N-(naphthalenylthioxomethyl)amino acid derivatives of K. Sestanj et al, U.S. Pat. No. 4,391,816, 1983; N-[(2-naphthalenyl)thioxomethyl]glycine derivatives of K. Sestanj, U.S. Pat. No. 4,447,452, 1984; and N-[[6-(lower alkoxy)-5-(trifluoromethylthio)-1-naphthalenyl]thioxomethyl]-N-(lower alkyl)-glycines of F. Bellini et al, U.S. Pat. No. 4,391,825, 1983, and N-[[5-(trifluoromethyl)-6-methoxy-1-naphthalenyl]thioxomethyl and carbonyl]-N-methylglycinamides of Bellini et al, U.S. Pat. No. 4,672,058, 1987. Accordingly, the present compounds represent an important new approach for the treatment of diabetes mellitus.

SUMMARY OF THE INVENTION

The N-naphthoylglycines of this invention are represented by formula (I)

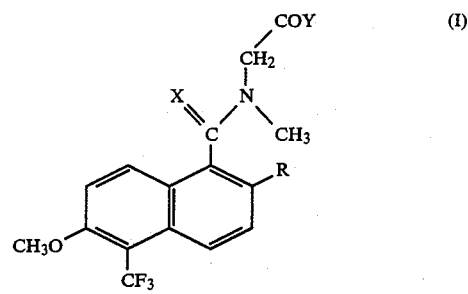

wherein R is halogen or lower alkoxy containing 1 to 5 carbon atoms, trifluoroethoxy, phenoxy or phenylmethoxy; X is =O or =S; Y is —OH, —NH2 or —NHCO2CH2CH3, and the pharmaceutically acceptable salts thereof.

Preferred compounds of the present invention are represented by formula (I) wherein R is fluorine, chlorine or bromine; X is =O or =S; Y is —OH, NH2 or —NHCO2CH2CH3, and the pharmaceutically acceptable salts thereof.

The most preferred compounds of the present invention are designated:
N-[(aminocarbonyl)methyl]-2-fluoro-6-methoxy-N-methyl-5-(trifluoromethyl)-1-naphthalenecarboxamide;
N-[2-[(ethoxycarbonyl)amino]-2-oxoethyl]-2-fluoro-6-methoxy-N-methyl-5-(trifluoromethyl)-1-naphthalenecarboxamide;
[[[2-fluoro-6-methoxy-5-(trifluoromethyl)-1-naphthalenyl]thioxomethyl]-methylamino]acetamide;
N-[[2-fluoro-6-methoxy-5-(trifluoromethyl)-1-naphthalenyl]carbonyl]-N-methylglycine;
N-[[2-fluoro-6-methoxy-5-(trifluoromethyl)-1-naphthalenyl]thioxomethyl]-N-methylglycine;
and the pharmaceutically acceptable salts thereof.

Also included in the present invention are the chemical intermediate compounds of formula (II)

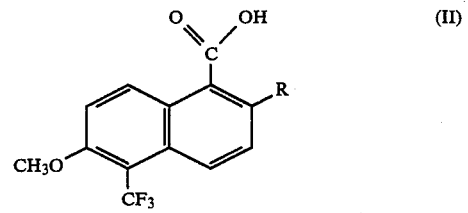

wherein R is as defined above.

The N-naphthoylglycines of the present invention can be prepared by the processes described hereinafter.

A method is provided for preventing or relieving diabetes mellitus associated complications in a diabetic mammal by administering to said mammal a prophylactic or alleviating amount of a compound of formula (I). Such complications include neuropathy, nephropathy, retinopathy and cataracts.

The compounds of formula (I), when admixed with a pharmaceutically acceptable carrier, form a pharmaceutical composition which can be used according to the preceding method.

DETAILED DESCRIPTION OF THE INVENTION

The compounds of this invention, represented by formula (I), can exist in rotameric forms. More explicitly, mesomerism imparts a partial double bond character to the carbonyl-nitrogen bonds. This partial double bond character leads to restricted rotation about the carbonyl-nitrogen bonds giving rise to cis and trans rotamers, the restricted rotation being augmented by the bulkiness of neighboring groups. The rotameric forms represented by structural formulas (I$^1$) and (I$^2$) are included within the scope of this invention:

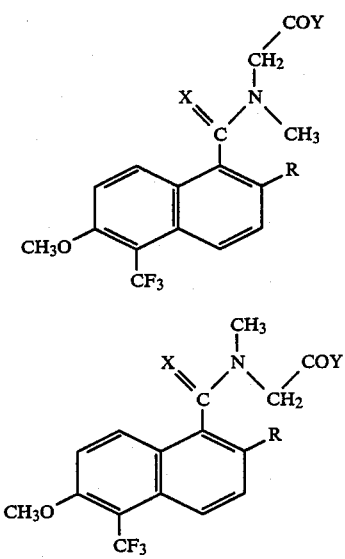

wherein R, X and Y are as defined above.

For brevity, the compounds of this invention, including their rotameric forms, are referred to herein as compounds of formula (I).

The compounds of formula (I) wherein Y is —OH form salts with suitable therapeutically acceptable inorganic and organic bases. These derived salts possess the same activity as their parent acid and are included within the scope of this invention. The acid is transformed in excellent yield into the corresponding therapeutically acceptable salt by neutralization of said acid with the appropriate inorganic or organic base. The salts are administered usually in the same manner as the parent acid compounds. Suitable inorganic bases to form these salts include, for example, the hydroxides, carbonates or bicarbonates of the therapeutically acceptable alkali metals or alkaline earth metals, for example, sodium, potassium, magnesium, calcium and the like. Suitable organic bases include the following amines: benzylamine; lower mono-, di- and trialkylamines, the alkyl radicals of which contain up to three carbon atoms, such as methylamine, dimethylamine, trimethylamine, ethylamine, di-and triethylamine, methylethylamine, and the like; mono-, di- and trialkanolamines, the alkanol radicals of which contain up to three carbon atoms, for example, mono-, di- and triethanolamine; alkylene-diamines which contain up to six carbon atoms, such as hexamethylenediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)-piperidine, as well as pyridine. Furthermore, there may be mentioned the corresponding quaternary salts, such as the tetraalkyl (for example tetramethyl), alkylalkanol (for example methyltriethanol and trimethylmonoethanol) and cyclic ammonium salts, for example the N-methylpyridinium, N-methyl-N-(2-hydroxyethyl)-morpholinium, N,N-dimethyl-morpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula (I) is dissolved in a suitable solvent of either moderate or low polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of lower polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

The N-naphthoylglycines of this invention may be administered to mammals, for example, man, monkeys or dogs, either alone or in dosage forms, i.e., capsules or tablets, combined with pharmacologically acceptable excipients.

Advantageously the compounds of this invention may be given orally. However, the method of administering the present active ingredients of this invention is not to be construed as limited to a particular mode of administration. For example, the compounds may be administered topically directly to the eye in the form of drops of sterile, buffered ophthalmic solutions, preferably of pH 7.2-7.6. Also, they may be administered orally in solid form containing such excipients as starch, milk sugar, certain types of clay and so forth. They may also be administered orally in the form of solutions or they may be injected parenterally. For parenteral administration they may be used in the form of a sterile solution, preferably of pH 7.2-7.6, containing a pharmaceutically acceptable buffer.

The dosage of the N-naphthoylglycines will vary with the form of administration. Furthermore, it will vary with the particular host under treatment. Generally, treatment is initiated with small dosages substantially less than the optimal dose of the compound. In general, the compounds of this invention are most desirably administered at a concentration level that will generally afford effective results without causing any harmful or deleterious side effects. For topical administration, a 0.05–1.8% solution may be administered dropwise in the eye. The frequency of instillation varies with the subject under treatment from a drop every two or three days to once daily. For oral or parenteral administration a preferred level of dosage ranges from about 0.5 mg to about 1000 mg per kilo of body weight per day, although aforementioned variations will occur. However, a dosage level that is in the range of from about 5.0 mg to about 60 mg per kilo of body weight per day is most satisfactory.

Unit dosage forms such as capsules, tablets, pills and the like may contain from about 25 mg to about 1250 mg of the active ingredients of this invention with a pharmaceutical carrier. Thus, for oral administration, capsules can contain from between about 25 mg to about 1250 mg of the active ingredients of this invention with or without a pharmaceutical diluent. Tablets, either effervescent or noneffervescent, can contain between about 25 to 1250 mg of the active ingredients of this invention together with conventional pharmaceutical carriers. Thus, tablets, which may be coated and either effervescent or noneffervescent may be prepared according to the known art. Inert diluents or carriers, for example, magnesium carbonate or lactose, can be used together with conventional disintegrating agents for example, magnesium stearate.

The N-naphthoylglycines can also be used in combination with insulin or oral hypoglycemic agents to produce a beneficial effect in the treatment of diabetes mellitus. In this instance, commercially available insulin preparations or oral hypoglycemic agents, exemplified by acetohexamide, chlorpropamide, tolazamide, tolbutamide and phenformin, are suitable. The compounds hereof can be administered sequentially or simultaneously with insulin or the oral hypoglycemic agent. Suitable methods of administration, compositions and doses of the insulin preparation or oral hypoglycemic agent are described in medical textbooks; for instance, "Physicians' Desk Reference", 36 ed., Medical Economics Co., Oradell, N.J. U.S.A., 1982. When used in combination, the N-naphthoylglycines are administered as described previously. The N-naphthoylglycines can be administered with the oral hypoglycemic agent in the form of a pharmaceutical composition comprising effective amounts of each agent.

The aldose reductase inhibiting effects of the compounds of formula (I) were tested by employing an in vitro testing procedure similar to that described by S. Hayman and J. H. Kinoshita, J. Biol. Chem., 240, 877 (1965). In the present case the procedure of Hayman and Kinoshita was modified in that the final chromatography step was omitted in the preparation of the enzyme from bovine lens. The results are tabulated in Table I under the heading IN VITRO.

The aldose reductase inhibiting property of the compounds of this invention and the utilization of the compounds in preventing, diminishing and alleviating diabetic complications by lowering polyol accumulation were also demonstrable in experiments using galactosemic rats, see Dvornik et al, Science, 182, 1146 (1973). Such experiments are exemplified hereinbelow after the listing of the following general comments pertaining to these experiments:

(a) Four or more groups of six male rats, 0–70 g, Sprague-Dawley strain, were used. The first group, the control group, was fed a mixture of laboratory chow (rodent Laboratory Chow, Purina) and glucose at 20% (w/w %) concentration. The untreated galactosemic group and the drug-treated groups were fed a similar diet in which galactose is substituted for glucose. The test compound was either admixed to the diet or administered by gavage. In experiments involving compound administration in the diet, the average dose administered was calculated from the actual food intake of the animals in each group. The concentration of galactose in the diet of the treated groups was the same as that for the untreated galactosemic group.

(b) After four days, the animals were killed by decapitation. The eyeballs were removed and punctured with a razor blade; the freed lenses were rolled gently on filter paper and weighed. The sciatic nerves were dissected as completely as possible and weighed. Both tissues when frozen can be kept up to two weeks before being analyzed for galactitol.

(c) The polyol determination was performed by a modification of the procedure of M. Kraml and L. Cosyns, Clin. Biochem., 2,373 (1969). Only two minor reagent changes were made: (a) the rinsing mixture was an aqueous 5% (w/v) trichloroacetic acid solution and (b) the stock solution was prepared by dissolving 25 mg of dulcitol in 100 mL of an aqueous trichloroacetic acid solution. [N.B.: For each experiment the average value found in the tissue from rats fed the glucose diet was subtracted from the individual values found in the corresponding tissue in galactose-fed rats to obtain the amount of polyol accumulated.]

A second in vivo model examined the effect of the compounds of the present invention on sorbitol accumulation in the tissues of 14-day streptozocin (STZ) (Upjohn) diabetic rats.

In each of the studies male Sprague-Dawley rats from Charles River Labs, Kingston, N.Y., weighing 200 to 250 g, were used. The animals were weighed and observed for 5 days prior to the start of the study.

In each study the rats were randomly assigned by weight into groups of 15 animals except for group I which contained 8 animals. The groups were treated as follows:

Group I: Control
Group II: STZ, 110 mg/kg i.p.
Group III: STZ, 110 mg/kg i.p. followed by the reference compound tolrestat 6 mg/day given daily by gavage for 14 days, beginning on the day of induction of diabetes.
Group IV: STZ, 110 mg/kg i.p. followed by various doses of a compound of the present invention given by gavage for 14 days, beginning on the day of induction of diabetes.

Following an overnight fast (water ad lib) the animals in groups II–IV were given by i.p. injection 110 mg STZ per kg body weight. The STZ was dissolved in cold citric acid, 0.03M, pH 4.5 and injected within 5 minutes of being dissolved. Control rats (group I) were injected with buffer only. One hour following the injection, standard laboratory chow (Rodent lab chow 5001, Purina) was placed in the cages.

Two days after STZ injection plasma glucose levels (from the tail vein) were determined following a 4 hour fast. Excluded from the study were animals whose plasma glucose was below 300 mg/dl. Control animals with plasma glucose levels greater than 200 mg/dl were also excluded.

On the morning of the 14th day following STZ injection the animals were fasted 4 hours prior to sacrificing by decapitation. The blood was collected into heparin containing tubes and placed on ice. Both lenses and sciatic nerves were removed immediately, weighed, frozen, and stored at $-20°$ C. until analyzed for sorbitol. The RBCs were collected by centrifugation, the plasma was removed and the cells were washed once with 10 volumes of cold saline. The washed packed RBCs were divided into 1 mL aliquots, extracted with cold perchloric acid and the acid extracts were stored at $-20°$ C. until analyzed for sorbitol.

The tabulated results in Table I show that the N-naphthoylglycines of this invention show the property that they diminish the accumulation of galactitol in the lenses and sciatic nerves of rats fed galactose. The figures under L, N, and D represent the percentage decrease of galactitol accumulation in the tissues of the lens, sciatic nerve, and diaphragm, respectively, for treated rats as compared to untreated rats.

Examination of the results tabulated in Table I below shows that the N-naphtholyglycines of this invention are well suited as aldose reductase inhibitors and they lower accumulation of sorbitol or galactitol in the diabetic or galactosemic rats. For example, N-[(aminocarbonyl)methyl]-2-fluoro-6-methoxy-5-(trifluoromethyl)-1-naphthalenecarboxamide at a dose of 10 mg/kg/day gives comparable results to N-[[6-methoxy-5-(trifluoromethyl)-1-naphthalenyl]thioxomethyl]-N-methylglycine at 9 mg/kg/day in the sciatic nerve. The latter compound is also known as tolrestat.

TABLE I

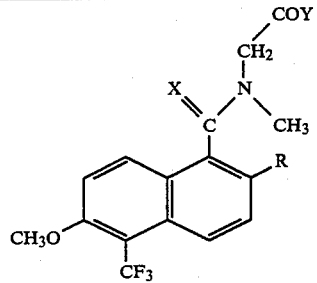

(I)

| Ex. | R¹ | X | Y | % Inhibition IN VITRO | | | | % Lowering dulcitol accumulation IN VIVO | | | |
|---|---|---|---|---|---|---|---|---|---|---|---|
| | | | | $10^{-5}$ M | $10^{-6}$ M | $10^{-7}$ M | $4 \times 10^{-8}$ M | mg/kg | (%) L | (%) N | (%) D |
| 1 | —F | =O | —NH₂ | 1 | 0 | N.D. | N.D. | 5 | N.S. | 39 | 32 |
| | | | | | | | | 10 | N.S. | 31 | 53 |
| | | | | | | | | 15 | N.S. | 42 | 57 |
| | | | | | | | | 10 | N.S. | 80 | 58 |
| | | | | | | | | 14 | N.S. | 64 | 62 |
| | | | | | | | | 24 | N.S. | 78 | 75 |
| | | | | | | | | 12 | N.S. | 66 | 52 |
| | | | | | | | | 19 | N.S. | 77 | 63 |
| | —F | =O | —NHCO₂C₂H₅ | 8 | 2 | N.D. | N.D. | 22 | N.S. | 80 | 55 |
| | —F | =S | —NH₂ | 2 | 6 | N.D. | N.D. | 2 | N.S. | N.S. | 53 |
| | | | | | | | | 5 | N.S. | 33 | 80 |
| | | | | | | | | 9.9 | N.S. | 54 | 87 |
| | —F | =O | —OH | 94 | 93 | 80 | 49 | 100 | 17 | N.D. | 89 |
| | | | | | | | | 52 | 15 | N.D. | 84 |
| | | | | | | | | 24 | N.S. | 68 | 70 |
| | | | | | | | | 16 | N.S. | 45 | 46 |
| | —F | =S | —OH | 99 | 94 | 86 | 45 | 25 | 23 | 92 | 93 |
| | | | | | | | | 4.8 | N.S. | N.S. | 86 |
| 2 | —Cl | =O | —NH₂ | 9 | 0 | N.D. | N.D. | 24 | N.S. | 62 | 53 |
| | —Cl | =O | —OH | 90 | 87 | 63 | 36 | 49 | N.S. | 83 | 80 |
| | | | | | | | | 26 | N.S. | 43 | 63 |
| 3 | —OCH₂CF₃ | =O | —OH | 96 | 91 | 67 | 32 | 50 | N.S. | 79 | 80 |
| | | | | | | | | 24 | N.S. | 37 | 63 |
| | —OCH₂CF₃ | =O | —NH₂ | 8 | 1 | N.D. | N.D. | 24 | N.S. | N.S. | N.S. |
| 4 | —OC₂H₅ | =S | —OH | 98 | 95 | 87 | 50 | 28 | N.S. | 46 | 85 |
| 5 | —OCH₂CF₃ | =S | —OH | 99 | 95 | 87 | 49 | 26 | N.S. | 33 | 88 |
| 6 | —OC₂H₅ | =O | —OH | 89 | 89 | 65 | 33 | 49 | N.S. | 45 | 57 |
| 7 | —O-n-C₃H₇ | =O | —OH | 92 | 86 | 46 | 21 | 50 | N.S. | 48 | 57 |
| 8 | —O—C₆H₅ | =O | —OH | 93 | 93 | 83 | 50 | 48 | N.S. | 32 | 67 |
| 9 | —Br | =O | —OH | 95 | 90 | 63 | N.D. | 97 | 8 | 44 | 84 |
| 10 | —Cl | =S | —OH | 95 | 91 | 81 | 51 | 24 | N.S. | N.S. | 90 |

TABLE I-continued

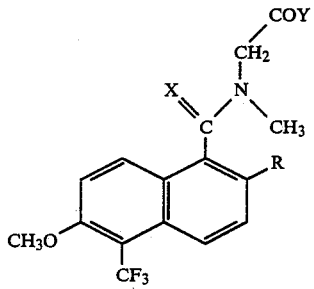

| Ex. | R¹ | X | Y | | | | | | | | |
|---|---|---|---|---|---|---|---|---|---|---|---|
| 11 | —O—⟨phenyl⟩ | =O | —OH | 96 | 94 | 89 | 49 | 24 | N.S. | N.S. | 83 |
| 12 | —O-n-C₄H₉ | =O | —OH | 92 | 88 | 42 | 25 | 49 | N.S. | N.S. | 55 |
|  | —O—CH₃ | =O | —OH | 99 | 95 | 91 | 56 | 26 | N.S. | N.S. | 71 |
|  | —O—CH₂—⟨phenyl⟩ | =S | —OH | 96 | 96 | 84 | 45 | 26 | N.S. | N.S. | 80 |
|  |  |  |  |  |  |  |  | 10 | N.S. | N.S. | 60 |
|  | —O—CH₃ | =O | —OH | 95 | 92 | 62 | 38 | 53 | N.S. | N.S. | N.S. |
| (tolrestat) |  |  |  | 98 | 94 | 65 | N.D. | 9 | N.S. | 58 | 87 |

N.S. = not significant
N.D. = not determined
L = lens
N = nerve
D = diaphragm

Two-Week Streptozocin - Diabetic Rat Model

| | | | | | % Lowering of Sciatic Nerve Polyol Accumulation | |
|---|---|---|---|---|---|---|
| Ex. | R¹ | X | Y | Dose (mg/kg) | Sorbital (%) | Fructose (%) |
| 1 | —F | =O | —NH₂ | 3 | 50 | 69 |
|  |  |  |  | 6 | 77 | 87 |
|  |  |  |  | 9 | 79 | 94 |
|  |  |  |  | 12 | 78 | 98 |
|  |  |  |  | 20 | 84 | 105 |
|  | Tolrestat |  |  | 6 | 53 | 58 |

The Process

The N-naphthoylglycines can be prepared by the following reaction schemes:

Scheme I

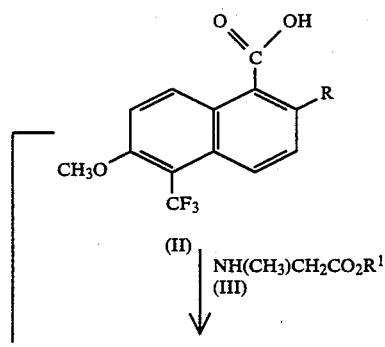

Scheme I
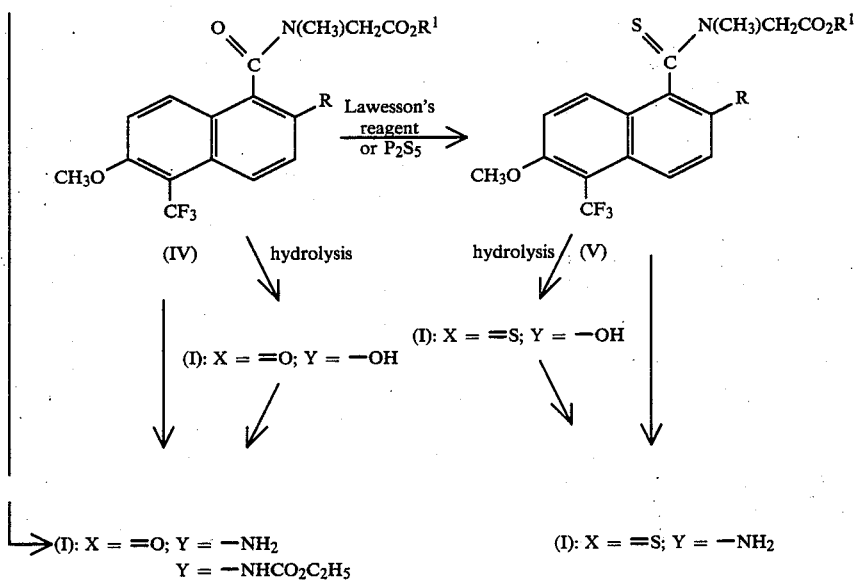
wherein R is as defined above, and $R^1$ is lower alkyl.
Scheme II
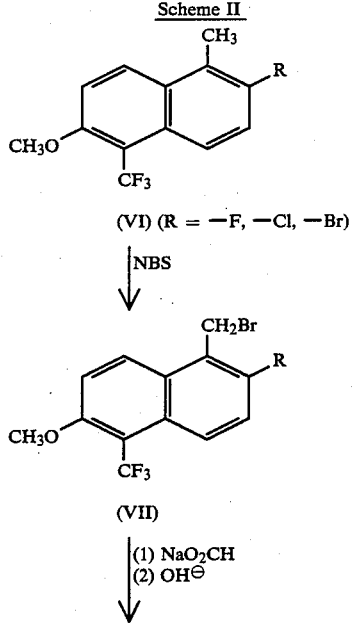
-continued
Schème II
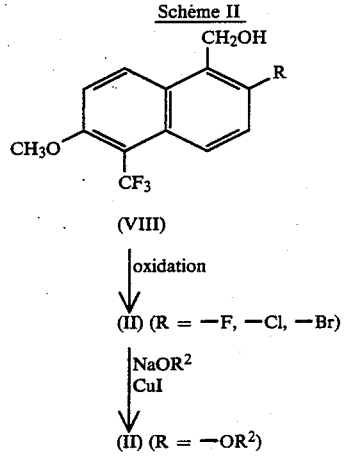
wherein R is as defined above, $OR^2$ is lower alkoxy, trifluoroethyl, phenoxy, or phenylmethoxy.
Scheme III
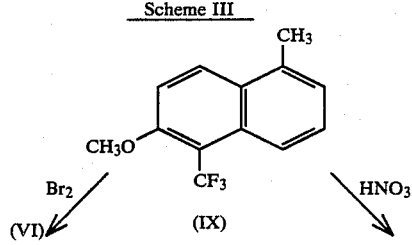

-continued
Scheme III

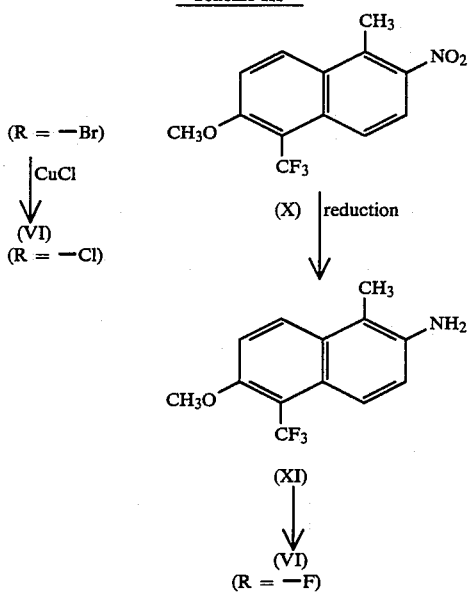

Referring to Scheme I, the naphthoic acids of formula (II) are converted to the carboxyl activated form. Description of carboxyl activating groups are found in general textbooks of peptide chemistry; for example, K. D. Kopple, "Peptides and Amino Acids," W. A. Benjamin, Inc., New York, 1966, pp 45–51, and E. Schröder and K. Lüoke, "The Peptides"; Vol. 1, Academic Press, New York, 1965; pp 77–128. Examples of the activated form of the carboxyl are the acid chloride, acid bromide, anhydride, azide, activated ester, or O-acyl urea obtained from a dialkylcarbodiimide. Preferred activated forms of the carboxyl are the acid chloride, the 1-benzotriazolyl, 2,4,5-trichlorophenyl, or succinimido activated esters.

Preferrably the carboxylic acid of formula (II) wherein R is defined herein is converted to a carboxyl activated form such as the acid chloride or the 1-benzotriazolyl ester. It is noted that the carboxyl activated form of formula (II) is not isolated in this process. The carboxyl activated form of formula (II) is then reacted with one to three molar equivalents of a sarcosine ester of formula (III) and with one to five equivalents of triethylamine to give the product of formula (IV) wherein $R^1$ is lower alkyl to give the amido ester of formula (IV) wherein R and $R^1$ are defined herein. The ester of formula (III) is used as its hydrohalide salt, preferrably the hydrochloride salt. The free amine of formula (III) is released upon treatment with base. The reaction is conveniently performed in an anhydrous solvent such as tetrahydrofuran or dimethylformamide at temperatures ranging from 15° C. to 40° C. and at times ranging from 2 to 24 hours.

The amido ester of formula (IV) wherein R and $R^1$ are defined herein is hydrolyzed to give the corresponding compound of formula (I) wherein R is defined herein and X is oxygen; or the thioxo ester of formula (V) wherein R and $R^1$ are defined herein is hydrolyzed to obtain the corresponding compound of formula (I) wherein R is defined herein and X is sulfur.

The hydrolysis of the esters of formula (IV) and (V) to give the corresponding product of formula (I) is most conveniently performed by employing a base as the hydrolyzing agent. The hydrolysis is performed in the presence of sufficient water, followed by acidification of the reaction mixture, to yield the desired acid. However, it should be understood that the manner of hydrolysis for the process of this invention is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1969, pp 615–617), or treatment with iodotrimethylsilane in carbon tetrachloride, or acetonitrile (see M. E. Jung et al, J. Am. Chem. Soc., 99, 968 (1977), also are applicable.

For basic hydrolysis, a preferred embodiment involves subjecting the ester to the action of a strong base, for example, sodium or potassium hydroxide, in the presence of sufficient water to effect hydrolysis of the ester. The hydrolysis is performed using a suitable solvent, for example, methanol, ethanol or tetrahydrofuran. The reaction mixture is maintained at a temperature of from about 25° C. to 50° C., or at the reflux temperature of the solvent employed until hydrolysis occurs. Usually from 10 minutes to 6 hours is sufficient for this hydrolysis. The reaction mixture is then rendered acidic with an acid, for example, acetic acid, hydrochloric acid, or sulfuric acid to release the free acid.

The thioxo ester of formula (V) is produced by reacting the amido ester of formula (IV) wherein R and $R^1$ are defined herein with phosphorus pentasulfide or Lawesson's reagent to give the corresponding thioxo ester of formula (V) wherein R and $R^1$ are defined herein.

The amide ester of formula (IV) can be reacted under anhydrous conditions with about two or five molar equivalents of phosphorus pentasulfide in an inert solvent, e.g., xylene or toluene, to obtain the corresponding thioxoester of formula (V). This reaction is performed conveniently at temperatures ranging from 80° C. to about 150° C., and at times ranging from 20 minutes to four hours. Preferably, the reaction is performed in the presence of an organic base for instance, N-ethyl morpholine, triethylamine, or pyridine.

Alternatively, the amide ester of formula (IV) can be reacted with Lawesson's reagent (0.6 to 2 eq) in an inert solvent such as toluene or xylenes at temperatures ranging from 80° C. to 130° C. for times ranging from 5 hours to 30 hours.

The esters of formula (IV) and (V) are converted directly to the corresponding amides of formula (I) wherein Y is —NH$_2$ and X is oxygen and sulfur respectively by reacting the compounds of formula (IV) and (V) with excess ammonia gas dissolved in an inert solvent such as methanol or THF at 0° C. to 65° C. for periods of 1 hour to 24 hours.

The compounds of formula (I) wherein X is oxygen and Y is —OH are converted to the ethoxycarbonyl amide compounds of formula (I) wherein X is oxygen and Y is —NHCO$_2$C$_2$H$_5$ by treating the compound of formula (I) with ethoxycarbonyl-t-butylcarbodiimide (1.0 to 2.0 eq) according to the procedure of O. Mitsunobu et al, Bull. Chem. Soc. Japan, 45, 3607 (1972) in an inert solvent such as THF heated from 40° C. to 80° C. for 1 to 24 hours.

Alternatively, the compounds of formula (I) wherein X is oxygen or sulfur and Y is —OH can be converted to the corresponding amide compounds of formula (I) wherein X is oxygen or sulfur and Y is —NH$_2$ by converting the carboxylic acid group of the compound of formula (I) to a carboxyl activated form as described herein above and reacting with ammonia (excess) in a solvent such as THF or aqueous ammonium hydroxide.

Referring to Scheme II, the compound of formula (VI) is converted to the compound of formula (VII) by reaction with N-bromosuccinimide (1 to 3 eq) with catalytic benzoyl peroxide (0.001 to 0.1 eq) in an inert solvent such as carbontetrachloride at temperatures ranging from 60° C. to 100° C. and at times ranging from 30 minutes to 40 hours.

The conversion of compound (VII) to compound (VIII) is carried out by reaction of (VII) with sodium formate (1 to 10 eq) in an aqueous alcoholic solvent at 50° C. to 100° C. for 30 minutes to 4 hours followed by an aqueous base work up (i.e. sodium or potassium hydroxide).

Other hydrolyzing conditions can be used such as sodium carbonate in aqueous alcohol.

For the conversion of (VIII) to (II) wherein R=—F, —Cl, —Br, excess chromium trioxide in sulfuric acid-water (a mixture known as Jones reagent) was used in acetone at temperatures from 0° C. to 30° C. at times ranging from 30 minutes to 4 hours.

Alternatively, excess potassium permanganate could be used as the oxidant in aqueous t-butyl alcohol at 70° C. to 100° C. for 30 minutes to 2 hours or in a biphasic mixture of toluene and water with catalytic amounts of tetra-N-butyl ammonium halide or 18-Crown-6 polyether at temperatures ranging from 20° C. to 100° C. and for times ranging from 1 hour to 4 days.

For the conversion of compound (II) wherein R=—Br to compound (II) wherein R=—OR$^2$, the compound (II) wherein R$^1$=—Br was treated with sodium-OR$^2$ which was generated by reacting HOR$^2$ with an equivalent amount of sodium hydride. Alternatively, sodium metal, potassium hydride, or potassium t-butoxide could be used to generate the metal alkoxide.

This metal alkoxide (1 to 15 eq) was reacted with the bromo acid compound (II), wherein R=—Br in the presence of copper (I), such as copper (I) iodide (1 to 15 eq). The reaction was done conveniently in THF solvent or in a polar aprotic solvent such as HMPA or DMF at temperatures ranging from 40° C. to 120° C. for 30 minutes to 6 hours.

Referring to Scheme III, the compound (IX) is converted to the compound (VI) wherein R=—Br by reaction with bromine (1 to 2 eq) in a solvent such as acetic acid or carbontetrachloride at 0° C. to 40° C. for times ranging from 1 hour to 30 hours.

The conversion of compounds of formula (VI) wherein R=—Br to compounds of formula (VI) wherein R=—Cl is carried out by reacting compound (VI) wherein R=—Br with copper (I) chloride (1 to 10 eq) in an inert polar aprotic solvent such as DMSO, DMF or HMPA at temperatures ranging from 150° C. to 250° C.

The compound (IX) was converted to the compound (X) by reacting the compound (IX) with fuming nitric acid (90% S.G.=1.5, 1 to 10 equivalents) in acetic anhydride at temperatures ranging from —20° C. to 25° C. and times ranging from 1 to 3 hours.

Other reagents that can be used are concentrated nitric acid (70%) at temperatures ranging from 0° C. to 30° C., and times ranging from 30 minutes to 1.5 hours, nitric acid in acetic acid at 25° C., sodium nitrate in trifluoroacetic acid at 0° C. and ammonium nitrate in trifluoroacetic anhydride at 25° C.

Reduction of compound (X) to (XI) is carried out by catalytic amounts of 10% palladium on carbon (5 to 20% by weight) in an alcoholic solvent or ethyl acetate at room temperature at 20 to 60 psi H$_2$ pressure. Alternatively, zinc in acid, iron powder or tin (II) chloride in acid can be used.

Conversion of compound (XI) to compound (VI) wherein R=—F is carried out with sodium nitrite (1 to 3 eq) in hydrogen fluoride-pyridine at temperatures ranging from —78° C. to 65° C. and times ranging from 30 minutes to 4 hours.

Alternatively, reaction of the amine (XI) with sodium nitrite (1 to 3 eq) in aqueous tetrafluoroboric acid at 0° C. to 30° C. for 20 minutes to 1 hour to provide the corresponding diazonium tetrafluoroborate (VI) wherein R=N$_2$+ BF$_4$−, which is then pyrollyzed neat or in an inert solvent such as xylenes or chlorobenzene at temperatures ranging from 100° C. to 200° C. and times ranging from 10 minutes to 1 hour.

The following Examples further illustrate this invention.

EXAMPLE 1

N-[(Aminocarbonyl)methyl]-2-fluoro-6-methoxy-N-methyl-5-(trifluoromethyl)-1-naphthalenecarboxamide (I): R=—F; X=═O; Y=—NH$_2$ Step (1) Preparation of N-[[2-Fluoro-6-methoxy-5-(trifluoromethyl)-1-naphthalenyl]carbonyl]-N-methylglycine, Methyl Ester 1-Hydroxybenzotriazole (5.08 g, 1.5 eq) and 1-(3-dimethylaminopropyl)-3-ethylcarbodiimide hydrochloride (5.76 g, 1.2 eq) were added to a mechanically stirred solution of 2-fluoro-6-methoxy-5-(trifluoromethyl)-1-naphthoic acid, prepared by the process of Example 13 (7.22 g, 25.05 mmol) in dry DMF (70 mL) at room temperature under a dry N$_2$ atmosphere. After 1 hour, a suspension of sarcosine methyl ester hydrochloride (7 g, 2 eq) in dry DMF (70 mL) was added. Triethylamine (11.4 mL) was immediately added and the suspension was stirred for 15 hours. The reaction mixture was added to rapidly stirred water (1.5 L) and this was extracted with ether (2×700 mL). Silica gel (50 mL) was added and the ether was removed. The silica gel-absorbate was flash chromatographed (3:2 petroleum ether:ethyl acetate) to provide the product as a white solid (7.9 g, 85%), m.p. 112.5°–114° C.

NMR (CDCl$_3$, 200 MHz, mixture of rotamers): δ2.90, 3.27 (2s, 3H, NCH$_3$), 3.56, 3.82 (2s, 3H, CO$_2$CH$_3$), 3.85 (d, 1H, NCH$^1$H$^2$—), 3.97 (s, 3H, OCH$_3$), 4.95 (d, 1H, NCH$^1$H$^2$), 7.3–7.5 (m, 2H, ArH), 8.0, 8.25 (2m, 2H, ArH);

IR (CHCl$_3$, cm$^{-1}$): 1745 (CO$_2$CH$_3$), 1645 (CON);

Anal. Calcd.: C, 54.70; H, 4.05; N, 3.75%. Found: C, 54.60; H, 3.86; N, 3.82%.

Step (2) Preparation of N-[[2-Fluoro-6-methoxy-5-(trifluoromethyl)-1-naphthalenyl]carbonyl]-N-methylglycine Aqueous sodium hydroxide (2.5N, 43 mL, 1.3 eq) was added to a stirred solution of N-[[2-fluoro-6-methoxy-5-(trifluoromethyl)-1-naphthalenyl]carbonyl]-1-methylglycine, methyl ester (3.1 g, 8.3 mmol) in 4:1 THF:methanol (50 mL) at room temperature. After 25 minutes, the THF:methanol was removed. Water (200 mL) was added and the aqueous solution was extracted with ether (150 mL). This ether extract was discarded. The aqueous phase was acidified to pH 1-3 with 10% aq HCl. The resulting white solid was collected and washed with water. The solid was then recrystallized from ethanol-water (first crop=1.77 g, second crop=0.71 g, combined yield 83%), m.p. 160°-161° C.

NMR (d$^6$DMSO, 400 MHz, mixture of rotamers): δ2.81, 3.16 (2s, 3H, NCH$_3$), 3.99, 4.02 (2s, 3H, OCH$_3$), 4.08 (d, 1H, J=17.2 Hz, NCH$^1$H$^2$), 4.56 (d, 1H, J=17.2 Hz, CH$^1$H$^2$), 7.62, 7.66 (2t, 1H, J=8.7 Hz, ArH), 7.73, 7.77 (2d, 1H, J=9.5 Hz, ArH), 8.17 (m, 1H, ArH), 7.94, 8.22 (2d, 1H, J=9.5 Hz, ArH);

IR (KBr, cm$^{-1}$): 3600–2700 (CO$_2$H), 1750, 1740 (CO$_2$H), 1640 (CON), 1615 (aromatic C-C);

MS (z/e): 359 (19%), 314 (17%), 271 (100%);

Anal. Calcd.: C, 54.70; H, 4.05; N, 3.75%. Found: C, 54.60; H, 3.86; N, 3.82%.

Step (3) Preparation of N-[2-[(Ethoxycarbonyl)amino]-2-oxoethyl]-2-fluoro-6-methoxy-N-methyl-5-(trifluoromethyl)-1-naphthalenecarboxamide According to the procedure of O. M. Mitsunobu et al, Bull. Chem. Soc. Japan, 45, 3607 (1972), a solution of ethoxycarbonyl-t-butylcarbodiimide (0.436, 1.10 q) and N-[[2-fluoro-6-methoxy-5-(trifluoromethyl)-1-naphthalenyl]carbonyl]-N-methylglycine (0.838 g, 2.38 mmole) in anhydrous THF (13.5 mL) was heated to reflux under a dry nitrogen atmosphere for 10 hours. The reaction was cooled to room temperature and the organic solvent was removed. The solid was flash chromatographed (1:1 pertroleum ether:ethyl acetate, silica). The resultant foam was triturated with petroleum ether and dried to provide the title compound as a white solid (0.567 g, 50%), m.p. 130°-132° C.

NMR (DMSO-d$^6$, 400 MHz): δ Product a mixture of rotamers, major rotamer reported first: 1.25, 1.08 (2t, 3H, J=7.1 Hz, CO$_2$CH$_2$CH$_3$), 7.79, 3.13 (2s, 3H, NCH$_3$), 4.17, 3.96 (2q, 2H, J=7.1 Hz, CO$_2$CH$_2$CH$_3$), 4.02, 3.99 (2s, 3H, ArOCH$_3$), 4.26 (d, 1H, J=17.5 Hz, NCH$^1$H$^2$CO$_2$), 4.86 (d, 1H, J=17.6 Hz, NCH$^1$H$^2$CO$_2$), 7.66, 7.62 (2t, 1H, J=9.4 Hz, ArH), 7.80, 7.72 (2d, 1H, J=9.5 Hz, ArH), 8.17 (m, 1H, ArH), 8.31, 7.94 (2d, 1H, J=9.5 Hz, ArH), 10.95, 10.51 (2s, 1H, NH);

IR (KBr, cm$^{-1}$): 1760 (C=O), 1718 (C=O), 1647 (C=O);

MS (CI): 431 (M+H, 100%), 411 (32%), 342 (53%);

Anal. Calcd.: C, 53.03; H, 4.22; N, 6.51%. Found: C, 53.36; H, 4.30; N, 6.17%.

Step (4) Preparation of N-[[2-Fluoro-6-methoxy-5-(trifluoromethyl)-1-naphthalenyl]thioxomethyl]-N-methylglycine, Methyl Ester A stirred suspension of N-[[2-fluoro-6-methoxy-5-(trifluoromethyl)-1-naphthalenyl]carbonyl]-N-methylglycine, methyl ester (4.54 g, 12.16 mmol), Lawesson's reagent (3.0 g, 0.6 eq) and toluene (45 mL) was heated to reflux under a dry N$_2$ atmosphere. Dissolution occurred. After 3 hours, more Lawesson's reagent (1.83 g, 0.37 eq) was added. After 19 hours the reaction mixture was cooled to room temperature and diluted with CH$_2$Cl$_2$. Silica gel was then added and the solvents were removed. The silica gel absorbate was flash chromatographed (3:2 dichloromethane:petroleum ether) to provide the product (4.6 g, 97%). A small portion was triturated with hexane to provide an off white solid, m.p. 108.5°-111° C. NMR (CDCl$_3$, 200 MHz, mixture of rotamers): δ3.12 and 3.60 (2s, 3H, NCH$_3$), 3.72 and 3.88 (2s, 3H, CO$_2$CH$_3$), 3.99 (s, 3H, OCH$_3$), 4.29 (d, 1H, J=16.8 Hz, NCH$^1$H$^2$), 5.64 (d, 1H, J=16.8 Hz, NCH$^1$H$^2$), 7.34 (t, 1H, J=9.3 Hz, ArH), 7.47 (d, 1H, J=9.9 Hz, ArH), 8.20 (m, 1H, ArH), 8.27 (d, 1H, J=9.9 Hz, ArH);

IR (CHCl$_3$, cm$^{-1}$): 1745 (CO$_2$CH$_3$);

Anal. Calcd.: C, 52.44; H, 3.88; N, 3.60%. Found: C, 52.19; H, 3.94; N, 3.69%.

Step (5) Preparation of N-[[2-Fluoro-6-methoxy-5-(trifluoromethyl)-1-naphthalenyl]thioxomethyl]-N-methylglycine Aqueous sodium hydroxide (2.5N, 5.5 mL, 1.16 eq) was added to a stirred solution of N-[[2-fluoro-6-methoxy-5-(trifluoromethyl)-1-naphthalenyl]thioxomethyl]-N-methylglycine, methyl ester (4.6 g, 11.81 mmol) in 3.8:1 THF:methanol at room temperature. After 20 minutes the organic solvents were removed. The solid was suspended in water (400 mL) and extracted with ether (100 mL). This extract was discarded. The aqueous phase was acidified to pH 1–3 with 10% aq HCl. The solid was filtered and washed with water. This solid was recrystallized from ethanol water as light yellow crystals (first crop 2.32 g, second crop 0.97 g, combined yield 74%), m.p. 179–190 (dec.).

NMR (d$^6$DMSO, 400 MHz): δ3.05 (s, 3H, NCH$_3$), 4.01 (s, 3H, OCH$_3$), 4.65 (d, 1H, J=16.8 Hz, NCH$^1$H$^2$), 5.23 (d, 1H, J=16.8 Hz, NCH$^1$H$^2$), 7.63 (t, 1H, J=9.4 Hz, ArH), 7.74 (d, 1H, J=9.5 Hz, ArH), 8.10 (m, 1H, ArH), 8.23 (d, 1H, J=9.5 Hz, ArH);

IR (KBr, cm$^{-1}$): 3650–2450 (CO$_2$H), 1710 (CO$_2$H);

MS (z/e): 375 (90%), 342 (50%), 311 (14%), 287 (100%);

Anal. Calcd.: C, 51.20; H, 3.49; N, 3.73%. Found: C, 50.89; H, 3.52; N, 3.74%.

Step (6) Preparation of [[[2-Fluoro-6-methoxy-5-(trifluoromethyl)-1-naphthalenyl]thioxomethyl]methylamino]acetamide 1-Hydroxybenzotriazole (0.84 g, 1.5 eq) and 1-(3-dimethylaminopropyl)-3-ethylcarbodiimide hydrochloride (0.96 g, 1.2 eq) were added to a stirred solution of N-[[2-fluoro-6-methoxy-5-(trifluoromethyl)-1-naphthalenyl]thioxomethyl]-N-methylglycine (1.50 g, 4.15 mmol) in anhydrous DMF (15 mL) at room temperature under a dry nitrogen atmosphere. After 1¾ hours, a saturated solution of ammonia in tetrahydrofuran (100 mL) was added to the reaction mixture at room temperature. After 1 hour, the reaction was cooled to 0° C. and ammonia gas was bubbled directly into the reaction mixture for 15 minutes. While still cool, the reaction mixture was filtered and the solid was washed with THF (2×10 mL). The solvent was removed from the filtrate and the residue was diluted with water (500 mL). The aqueous phase was extracted with ether (6×100 mL). The extracts were combined and preabsorbed onto silica gel. The absorbate was flash chromatographed (19:1 chloroform:methanol, silica) and the resulting product was re-flash chromatographed (chloroform to 49:1 chloroform:methanol, silica) to provide the title compound as a light yellow solid (0.30 g, 20%), m.p. 222°-224° C.

NMR (DMSO-d$^6$, 400 MHz): δ3.02 (s, 3H, NCH$_3$), 4.01 (s, 3H, ArOCH$_3$), 4.37 (d, 1H, J=15.9 Hz, NCH$^1$H$^2$CONH$_2$), 5.34 (d, 1H, J=15.8 Hz, NCH$^1$H$^2$CONH$_2$), 7.26 (s, 1H, CONH$^1$H$^2$), 7.62 (t, 1H, J=9.2 Hz, ArH), 7.71 (m, 2H, ArH and CONH$^1$H$^2$), 8.08 (m, 1H, ArH), 8.40 (d, 1H, J=9.5 Hz, ArH);

IR (KBr, cm$^{-1}$): 3388 (NH), 3292 (NH), 1667 (C=O), 1604 (C=C), 1512 (C=S);

MS (CI): 375 (M+H, 87%), 358 (100%), 355 (60%), 287 (17%);

Anal. Calcd.: C, 51.33; H, 3.77; N, 7.48%. Found: C, 51.20; H, 3.96; N, 7.28%.

Step (7) Preparation of N-[(Aminocarbonyl)methyl]-2-fluoro-6-methoxy-N-methyl-5-(trifluoromethyl)-1-naphthalenecarboxamide Ammonia gas was bubbled into methanol (40 mL) contained in a 250 mL pressure bottle at 0° C. for 30 minutes. N-[[2-Fluoro-6-methoxy-5-(trifluoromethyl)-1-naphthalenyl]carbonyl]-N-methylglycine, methyl ester (2.05 g. 5.49 mmole) was added to the reaction vessel which was then sealed and warmed to room temperature. After 1½ hours, the reaction was heated to 65° C. After 6 hours of heating, the reaction was cooled to room temperature and the methanol was removed. The crude product was flash chromatographed (19:1 chloroform:methanol, silica) then recrystallized in chloroform to provide the product as a white powder (1.32 g, 67%), m.p. 171°-172° C.

NMR (CDCl$_3$, 400 MHz): δ product is a 7:1 mixture of rotamers; major rotamer reported first: 2.98, 3.32 (2s, 3H, NCH$_3$), 4.01, 4.00 (2s, 3H, ArOCH$_3$), 4.22 (d, 1H, J=15.5 Hz, NCH$^1$H$^2$CO$_2$H), 4.47 (d, 1H, J=15.5 Hz, NCH$^1$H$^2$CO$_2$H), 5.54 (broad s, 1H, CONH$^1$H$^2$), 6.19 (broad s, 1H, CONH$^1$H$^2$), 7.38 (t, 1H, J=9.7 Hz, ArH), 7.45 (d, 1H, J=9.4 Hz, ArH), 8.01, 7.90 (2d, 1H, J=9.4 Hz, ArH), 8.29 (q, 1H, J=3.2 Hz, ArH);

IR (KBr, cm$^{-1}$): 3405 (NH), 1678 (CONH$_2$), 1655 (CON).

MS (z/e): 358 (6%), 341 (6%), 271 (100%), 200 (34%), 195 (30%);

Anal. Calcd.: C, 53.64; H, 3.94; N, 7.83%. Found: C, 53.95; H, 3.59; N, 7.57%.

EXAMPLE 2

[[[2-Chloro-6-methoxy-5-(trifluoromethyl)-1-naphthalenyl]carbonyl]methylamino]acetamide (I): R=—Cl; X=O; Y=—NH$_2$ Step (1) Preparation of N-[[2-Chloro-6-methoxy-5-(trifluoromethyl)-1-naphthalenyl]carbonyl]-N-methylglycine, Methyl Ester 1-Hydroxybenzotriazole (7.11 g, 1.5 eq) and 1-(3-dimethylaminopropyl)-3-ethylcarbodiimide hydrochloride (8.07 g, 1.2 eq) were added to a stirred solution of 2-chloro-6-methoxy-5-(trifluoromethyl)naphthoic acid, prepaired by the process of Example 15 (10.69 g, 0.0351 mole) in dry DMF (98 mL) at room temperature under a dry nitrogen atmosphere. After 1¼ hours a suspension of sarcosine methyl ester hydrochloride (9.80 g, 0.0702 mole, 2 eq) in dry DMF (98 mL) was added to the reaction mixture followed by the addition of dry triethylamine (16 mL, 3.2 eq). After 3 hours, the reaction mixture was diluted with water (3 L) and the resulting suspension was stirred rapidly. The tan solid was collected, washed with water and purified by flash chromatography (eluant 60/40 petroleum ether/EtOAc) to provide a foam (5.54 g, 41%). A small portion was again flash chromatographed (50/50 petroleum ether/EtOAc) and the resulting colorless oil triturated with petroleum ether to give an analytical sample as a white solid, m.p. 103°-170° C.

NMR (CDCl$_3$, 200 MHz): δ2.90 (s, 3H, NCH$_3$), 3.89 (s, 3H, COOCH$_3$), 3.89 (d, 1H, J=17 Hz, NCH$^1$H$^2$), 4.04 (s, 3H, OCH$_3$), 5.05 (d, 1H, J=17 Hz, NCH$^1$H$^2$), 7.46-7.57 (m, 2H, ArH), 8.25 (t, 2H, J=10 Hz, ArH);

IR (CHCl$_3$, cm$^{-1}$): 1740 (CO$_2$CH$_3$) 1640 (CON);

MS (Exact Mass) Calcd.: 389.0653 Found: 389.0675.

Step (2) Preparation of N-[[2-Chloro-6-methoxy-5-(trifluoromethyl)-1-naphthalenyl]carbonyl]-N-methylglycine Sodium hydroxide (2.5N, 2.3 mL, 1.2 eq) was added to a stirred solution of N-[[2-chloro-6-methoxy-5-(trifluoromethyl)-1-naphthalenyl]carbonyl]-N-methylglycine, methyl ester (2.10 g, 5.29 mmole) in THF (18 mL) and methanol (18 mL) at room temperature under an atmosphere of nitrogen. After stirring 1½ hours the organic solvents were removed. The residue was slurried in water (~300 mL) and extracted with ether (600 mL). The extracts were discarded. The aqueous mixture was acidified to pH 1 with 10% HCl. The organic oil was extracted with ethyl acetate (3×100 mL). The extracts were combined, dried over magnesium sulfate, filtered and the ethyl acetate was removed. The sample was purified by recrystallizing once from ethanol/water and once from chloroform/petroleum ether to give the analytically pure product as a white crystalline solid (0.90 g, 45%), m.p. 157°-159° C.

NMR (d$^6$DMSO, 400 MHz): δ4.03 (s, 3H, —OCH$_3$), 4.05 (d, 1H, J=17 Hz, NCH$^1$H$^2$), 4.59 (d, 1H, J=17 Hz, NCH$^1$H$^2$), 7.74 (d, 1H, J=10 Hz, ArH), 7.75 (d, 1H, J=10 Hz, ArH), 8.10 (d, 1H, J=12 Hz, ArH), 8.25 (d, 1H, J=10 Hz, ArH);

IR (KBr, cm$^{-1}$): 3600-2500 (CO$_2$H), 1755 (CO$_2$CH$_3$), 1620 (CON), 1515 (C=C);

MS (z/e): 375 (8.5%), 289 (14%), 287 (34%), 216 (11%), 168 (14%), 111 (19%), 95 (26%), 86 (100%), 79 (31%);

Anal. Calcd.: C, 51.15; N, 3.76; N, 3.73%. Found: C, 51.20; N, 4.11; N, 3.99%.

Step (3) Preparation of [[[2-Chloro-6-methoxy-5-(trifluoromethyl)-1-naphthalenyl]carbonyl]methylamino]acetamide Ammonia gas was bubbled into methanol (40 mL) contained in a 250 mL pressure bottle at 0° C. for 30 minutes. N-[[2-Chloro-6-methoxy-5-trifluoromethyl)-1-naphthalenyl]carbonyl]-N-methylglycine, methyl ester (1.9 g, 4.87 mmol) was added to the reaction vessel which was then sealed and warmed to room temperature. After 1½ hours the reaction was heated to 65° C. After 8 hours of heating the reaction was cooled to room temperature and the methanol was removed. The crude product was flash chromatographed (19/1 chloroform/methanol, silica) to provide the product as a white solid (1.52 g, 83.5%), m.p. 196°-198° C.

NMR (d$^6$DMSO, 400 MHz): δ2.73 (s, 3H, NCH$_3$), 3.76 (d, 1H, J=16 Hz, NCH$^1$H$^2$), 4.03 (s, 3H, OCH$_3$), 4.62 (d, 1H, J=16 Hz, NCH$^1$H$^2$), 7.16 (broad s, 1H, CONH$^1$H$^2$), 7.59 (broad s, 1H, CONH$^1$H$^2$), 7.72 (d, 1H, J=4 Hz, ArH), 7.74 (d, 1H, J=4 Hz, ArH), 8.09 (d, 1H, J=10 Hz, ArH), 8.46 (d, 1H, J=10 Hz, ArH);

IR (KBr, cm$^{-1}$): 3340 (NH), 1700 (C=O), 1620 (C=O);

MS (z/e): 376 (5%), 374 (15%), 289 (32%), 287 (100%), 261 (20%), 71 (26%);

Anal. Calcd.: C, 51.28; H, 3.76; N, 7.47%. Found: C, 51.03; H, 3.98; N, 7.41%.

EXAMPLE 3

N-[[6-Methoxy-2-(2,2,2-trifluoroethoxy)-5-(trifluoromethyl)-1-naphthalenyl]carbonyl]-N-methylglycine (I): R=—O—CH$_2$—CF$_3$; X=O; Y=—NH$_2$ Step (1) Preparation of N-[[6-Methoxy-2-(2,2,2-trifluoroethoxy)-5-(trifluoromethyl)-1-naphthalenyl]carbonyl]-N-methylglycine, Methyl Ester 1-Hydroxybenzotriazole (5.05 g, 1.5 eq) and 1-(3-dimethylaminopropyl)-3-ethylcarbodiimide (5.74 g, 1.2 eq) were added to a stirred solution of 6-methoxy-2-(2,2,2-trifluoroethoxy)-5-(trifluoromethyl)naphthoic acid, prepared by the process of Example 14 (9.18 g, 24.9 mmol) in anhydrous DMF (90 mL) at room temperature under a dry nitrogen atmosphere. After 1¼ hours, a suspension of methyl sarcosinate hydrochloride (6.96 g, 2.0 eq) in anhydrous DMF (40 mL) was added to the reaction followed by triethylamine (11.12 mL, 3.2 eq). After 30 minutes, the reaction was diluted with water (1.5 L) and extracted with ether (3×250 mL). The extracts were combined, dried with magnesium sulfate, and the ether was removed. The crude product was flash chromatographed (13:7→1:1 petroleum ether:ethyl acetate, silica) to provide the product as a clear oil (9.15 g, 81%). A small sample was triturated in petroleum ether to provide a white solid for analysis, m.p. 91.5°–93° C.

NMR (CDCl$_3$, 200 MHz): $\delta$2.85 (s, 3H, NCH$_3$), 3.83 (s, 3H, CO$_2$CH$_3$), 3.87 (d, 1H, J=15.6 Hz, NCH$^1$H$^2$CO$_2$—), 3.98 (s, 3H, ArOCH$_3$), 4.49 (q, 2H, J=7.7 Hz, OCH$_2$CF$_3$), 4.95 (d, 1H, J=17.5 Hz, NCH$^1$H$^2$CO$_2$), 7.29 (d, 1H, J=9.5 Hz, ArH), 7.42 (d, 1H, J=9.3 Hz, ArH), 8.17 (d, 1H, J=9.5 Hz, ArH), 8.25 (d, 1H, J=10.0 Hz, ArH);

IR (CHCl$_3$, cm$^{-1}$): 3016 and 2960 (CH), 1746 (C=O), 1640 (CON), 1608 (C=C);

Anal. Calcd.: C, 50.34; H, 3.78; N, 3.09%. Found: C, 50.48; H, 3.47; N, 3.01%.

Step (2) Preparation of N-[[6-Methoxy-2-(2,2,2-trifluoroethoxy)-5-(trifluoromethyl)-1-naphthalenyl]carbonyl]-N-methylglycine Methanol (15.0 mL) and sodium hydroxide solution (2.5N, 2.86 mL, 1.1 eq) were added to a stirred solution of N-[[6-methoxy-2-(2,2,2-trifluoroethoxy)-5-(trifluoromethyl)-1-naphthalenyl]carbonyl]-N-methylglycine (2.95 g, 6.51 mmole) in THF (30.0 mL) at room temperature. After 45 minutes the organic solvents were removed and the residue was dissolved in saturated aqueous sodium bicarbonate solution (125 mL). The basic phase was extracted with ether (1×50 mL), the extract was discarded. The basic phase was diluted with water (75 mL) and acidified to pH 1 with concentrated hydrochloric acid. The acidic phase was extracted with ether (3×50 mL). The extracts were combined, washed with saturated aqueous sodium chloride (1×50 mL), dried with sodium sulfate, and the ether was removed. The crude product was recrystallized from chloroform:hexane as a white powder (1.03 g, 36%), m.p. 158°–160° C.

NMR (d$^6$DMSO, 400 MHz): $\delta$ product a mixture of rotamers: major rotamer reported first: 2.75, 3.13 (2s, 3H, NCH$_3$), 3.96 (d, 1H, J=17.1 Hz, NCH$^1$H$^2$CO$_2$H), 4.00, 3.97 (2s, 3H, ArOCH$_3$), 4.58 (d, 1H, J=17.1 Hz, NCH$^1$H$^2$CO$_2$H), 4.95 (m, 2H, OCH$_2$CF$_3$), 7.69 (m, 2H, ArH), 8.14 (m, 2H, ArH);

IR (KBr, cm$^{-1}$): 1728 (C=O), 1637 (CON), 1610 and 1589 (C=C);

MS (z/e): 439 (14%), 351 (68%), 268 (41%), 225 (46%), 197 (64%), 182 (73%), 169 (100%);

Anal. Calcd.: C, 49.21; H, 3.44; N, 3.19%. Found: C, 49.16; H, 3.80; N, 3.30%.

Step (3) Preparation of N-[[6-Methoxy-2-(2,2,2-trifluoroethoxy)-5-(trifluoromethyl)-1-naphthalenyl]carbonyl]-N-methylglycine A solution of N-[[6-methoxy-2-(2,2,2-trifluoroethoxy)-5-(trifluoromethyl)-1-naphthalenyl]carbonyl]-N-methylglycine, methyl ester (2.56 g, 5.65 mmole) in methanol (10 mL) was added to a stirred methanolic solution of ammonia gas in a pressure bottle at room temperature. After 1½ hours, the reaction was heated to 65° C. After 8 hours the reaction was cooled to room temperature and the methanol was removed. The crude product was purified by flash chromatography (19:1 chloroform:methanol, silica) then recrystallized in chloroform:hexane to provide the product as a white powder (1.79 g, 72%), m.p. 162°–164° C.

NMR (DMSO-d$^6$, 400 MHz): $\delta$ product is a 4:1 mixture of rotamers: major rotamer reported first: 2.72, 3.08 (2s, 3H, NCH$_3$), 3.71 (m, 1H, NCH$^1$H$^2$CONH$_2$), 3.99, 3.97 (2s, 3H, ArOCH$_3$), 4.60 (d, 1H, J=15.2 Hz, NCH$^1$H$^2$CONH$_2$), 4.94 (m, 2H, OCH$_2$CF$_3$), 7.15 (s, 1H, CONH$^1$H$^2$), 7.46, 6.89 (2s, 1H, CONH$^1$H$^2$), 7.67 (m, 2H, 2ArH), 8.10 (d, 1H, J=8.0 Hz, ArH), 8.30, 7.98 (2d, 1H, J=9.7 Hz, ArH);

IR (KBr, cm$^{-1}$): 3500 (NH$_2$), 1682 (C=O), 1620 (C=O);

MS (CI): 439 (M+H, 77%), 422 (100%), 419 (48%), 351 (40%);

Anal. Calcd.: C, 49.32; H, 3.68; N, 6.39%. Found: C, 49.12; H, 3.37; N, 6.54%.

EXAMPLE 4

N-[[2-Ethoxy-6-methoxy-5-(trifluoromethyl)-1-naphthalenyl]thioxomethyl]-N-methylglycine (I): R=—O—CH$_2$—CH$_3$; X==S; Y=—OH Step (1) Preparation of N-[[2-Ethoxy-6-methoxy-5-(trifluoromethyl)-1-naphthalenyl]thioxomethyl]-N-methylglycine, Methyl Ester N-[[2-Ethoxy-6-methoxy-5-(trifluoromethyl)-1-naphthalenyl]carbonyl]-N-methylglycine, methyl ester (2.39 g, 5.98 mmol) prepared by the process of Example 6, step 2, and Lawesson's reagent (1.6 g, 0.66 eq) were added to toluene (35 mL) and the suspension was heated to reflux under a dry N$_2$ atmosphere where dissolution occured. After 6 hours, more Lawesson's reagent (1.5 g) was added and the solution was heated for an additional 16 hours. The reaction mixture was cooled to room temperature and CH$_2$Cl$_2$ (100 mL) was added. Silica gel (25 mL) was then added and the solvents were removed. The silica absorbate was flash chromatographed (gradient 9:1 CH$_2$Cl$_2$: petroleum ether to petroleum ether to 7:3 petroleum ether:ethyl acetate, silica) to provide the product as an off white solid (1.85 g, 75%). A small portion was recrystallized from petroleum ether, m.p. 104°–107° C.

NMR (CDCl$_3$, 200 MHz): $\delta$1.40 (t, 3H, J=7.0 Hz, OCH$_2$CH$_3$), 3.07 (s, 3H, NCH$_3$), 3.87 (s, 3H, CO$_2$CH$_3$), 3.95 (s, 3H, OCH$_3$), 4.23 (q, 2H, J=7.0 Hz, OCH$_2$CH$_3$), 4.22 (d, 1H, J=16.4 Hz, NCH$^1$H$^2$), 5.52 (d, 1H, J=16.4 Hz, NCH$^1$H$^2$), 7.31 (m, 2H, ArH), 8.17 (m, 2H, ArH);

IR (CHCl$_3$, cm$^{-1}$): 1745 (CO$_2$CH$_3$);

Anal. Calcd.: C, 54.93; H, 4.85; N, 3.37%. Found: C, 54.96; H, 4.55; N, 3.30%.

Step (2) Preparation of N-[[2-Ethoxy-6-methoxy-5-(trifluoromethyl)-1-naphthalenyl]thioxomethyl]-N-methylglycine Aqueous sodium hydroxide (2.5N, 2.0 mL, 5 mmol) was added to a stirred, room temperature solution of N-[[2-ethoxy-6-methoxy-5-(trifluoromethyl)-1-naphthalenyl]thioxomethyl]-N-methylglycine, methyl ester (1.77 g, 4.26 mmol), in 5:1 THF:methanol (20 mL). After 30 minutes, the organic solvents were removed. Water (150 mL) was added and the aqueous phase was extracted with ether (2×60 mL). The ether phase was discarded. The aqueous phase was acidified to pH 1–3 and the yellow solid was collected. This solid was recrystallized from ethanol:water with a hot filtration to provide a yellow solid (1.11 g, 53%). This solid was recrystallized from petroleum ether:chloroform with a hot filtration to provide the title compound (0.91 g), m.p. 180°–182° C.

NMR (DMSO-$d^6$, 400 MHz): δ1.29 (t, 3H, J=6.9 Hz, OCH$_2$CH$_3$), 2.99 (s, 3H, NCH$_3$), 3.97 (s, 3H, OCH$_3$), 4.22 (q, 2H, J=6.9 Hz, OCH$_2$CH$_3$), 4.57 (d, 1H, J=16.7 Hz, NCH$^1$H$^2$), 5.27 (d, 1H, J=16.7 Hz, NCH$^1$H$^2$), 7.59 (m, 2H, ArH), 8.03 (dm, 1H, ArH), 8.14 (d, 1H, J=8.4 Hz, ArH);

IR (KBr, cm$^{-1}$): 3250–2350 (CO$_2$H), 1720 (CO$_2$H);

MS (z/e): 401 (39%), 368 (100%), 313 (11%);

Anal. Calcd.: C, 53.86; H, 4.52; N, 3.49%. Found: C, 53.92; H, 4.55; N, 3.54%.

EXAMPLE 5

N-[[6-Methoxy-2-(2,2,2-trifluoroethoxy)-5-(trifluoromethyl)-1-naphthalenyl]thioxomethyl]-N-methylglycine (I): R=—O—CH$_2$—CF$_3$; X==S; Y=—OH Step (1) Preparation of N-[[6-Methoxy-2-(2,2,2-trifluoroethoxy)-5-(trifluoromethyl)-1-naphthalenyl]thioxomethyl]-N-methylglycine, Methyl Ester Lawesson's reagent (3.20 g, 0.6 eq) was added to a stirred solution of N-[[6-methoxy-2-(2,2,2-trifluoroethoxy)-5-(trifluoromethyl)-1-naphthalenyl]carbonyl]-N-methylglycine, methyl ester, prepared by the process of Example 3, Step 1 (6.00 g, 13.2 mmol) in toluene (60 mL) at room temperature under argon. The reaction was heated to reflux for 11½ hours, with more Lawesson's reagent (4.8 g, 0.9 eq) added in two portions after 2¼ and 8¾ hours. The reaction was cooled to room temperature and diluted with methylene chloride (300 mL). The crude reaction mixture was preabsorbed onto silica gel and flash chromatographed (petroleum ether→7:3 petroleum ether:ethyl acetate eluent gradient, silica) to provide the product as a yellow foam (3.94 g, 64%). A small sample was washed with petroleum. The filtrate was evaporated to dryness to provide a yellow solid for analysis, m.p. 104°–105° C.

NMR (CDCl$_3$, 200 MHz): δ3.06 (s, 3H, NCH$_3$), 3.87 (s, 3H, CO$_2$CH$_3$), 3.96 (s, 3H, ArOCH$_3$), 4.28 (d, 1H, J=16.8 Hz, NCH$^1$H$^2$CO$_2$), 4.51 (t, 2H, J=7.9 Hz, OCH$_2$CF$_3$), 5.60 (d, 1H, J=16.8 Hz, NCH$^1$H$^2$CO$_2$), 7.28 (d, 1H, J=9.8 Hz, ArH), 4.41 (d, 1H, J=9.1 Hz, ArH), 8.20 (m, 2H, 2ArH);

IR (CHCl$_3$, cm$^{-1}$): 2978 (CH), 1749 (C=O), 1622 and 1604 (C=C);

Anal. Calcd.: C, 48.62; H, 3.65; N, 2.98%. Found: C, 48.56; H, 3.78; N, 3.11%.

Step (2) Preparation of N-[[6-Methoxy-2-(2,2,2-trifluoroethoxy)-5-(trifluoromethyl)-1-naphthalenyl]thioxomethyl]-N-methylglycine Methanol (17 mL) and sodium hydroxide (2.5N, 3.60 mL, 1.1 eq) were added to a stirred solution of N-[[6-methoxy-2-(2,2,2-trifluoroethoxy)-5-(trifluoromethyl)-1-naphthalenyl]thioxomethyl]-N-methylglycine, methyl ester (3.82 g, 8.16 mmol) in THF (35 mL) at room temperature. After 2 hours, the organic solvents were removed and the residue was dissolved in saturated aqueous sodium bicarbonate (125 mL). The basic phase was extracted with ether (1×50 mL), the extracts was discarded. The basic phase was diluted with water (75 mL) and acidified to pH 1 with concentrated hydrochloric acid. The acidic phase was extracted with ether 3×50 mL). The extracts were combined, washed with saturated aqueous sodium chloride (1×50 mL), dried with sodium sulfate, and the ether was removed. The crude product was recrystallized from chloroform to provide the product as a white powder (1.82 g, 49%), m.p. 194°–196° C. (dec.).

NMR (CDCl$_3$, 400 MHz): δ3.16 (s, 3H, NCH$_3$), 3.99 (s, 3H, ArOCH$_3$), 4.56 (m, 3H, OCH$_2$CF$_3$ and NCH$^1$CO$_2$H), 5.55 (d, 1H, J=17.0 Hz, NCH$^1$H$^2$CO$_2$H), 7.32 (d, 1H, J=9.6 Hz, ArH), 7.42 (d, 1H, J=9.1 Hz, ArH), 8.18 (d, 1H, J=9.6 Hz, ArH), 8.24 (d, 1H, J=9.1 Hz, ArH);

IR (KBr, cm$^{-1}$): 1745 (C=O), 1603 (C=C);

MS (z/e): 455 (100%), 422 (55%), 367 (64%);

Anal. Calcd.: C, 47.48; H, 3.32; N, 3.07%. Found: C, 47.24; H, 3.53; N, 2.99%.

EXAMPLE 6

N-[[2-Ethoxy-6-methoxy-5-(trifluoromethyl)-1-naphthalenyl]carbonyl]-N-methylglycine (I): R=—O—CH$_2$—CH$_3$; X==O; Y=—OH Step (1) Preparation of 2-Ethoxy-6-methoxy-5-(trifluoromethyl)naphthoic acid Absolute ethanol (8.1 mL, 12 eq) was added over a 5 minute period to a stirred, room temperature suspension of sodium hydride (7.3 g, 13 eq, 50% dispersion in mineral oil) in dry THF (30 mL). After gas evolution ceased, copper (I) iodide (13.2 g, 13 eq) and a solution of 2-bromo-6-methoxy-5-trifluoromethyl-1-naphthoic acid, prepared in Example 14, Step 2 (4.05 g, 11.6 mmol) in dry THF (20 mL) were added slowly to avoid excessive foaming. The dark green reaction mixture was then heated to reflux for 2.5 hours. The reaction mixture was cooled to room temperature and added to water (1 L). Ether (600 mL) was added and the reaction mixture was acidified with concentrated HCl and stirred for 10 minutes. The biphasic mixture was filtered through celite and the celite was washed with ether (100 mL) and ethyl acetate (100 mL). The layers were separated and the organic layer was washed with saturated aqueous NaCl and dried (MgSO$_4$). The solvent was removed and the gummy solid was triturated with petroleum ether. The resulting solid was dried in vacuo (2.66 g, 74%). A small portion was recrystallized from ethanol water with a hot filtration to give an off white solid, m.p. 178°–180° C.

NMR (CDCl$_3$, 200 MHz): δ1.52 (t, 3H, J=4.8 Hz, —OCH$_2$CH$_3$), 3.99 (s, 3H, OCH$_3$), 4.35 (q, 2H, J=4.8, —OCH$_2$CH$_3$), 7.39 (m, 2H, ArH), 8.34 (dm, 1H, ArH), 8.77 (d, 1H, ArH);

IR (KBr, cm$^{-1}$): 3400–2700 (CO$_2$H), 1710 (CO$_2$H);

Anal. Calcd.: C, 57.33; H, 4.17%. Found: C, 57.68; H, 4.42%.

Step (2) Preparation of N-[[2-Ethoxy-6-methoxy-5-(trifluoromethyl)-1-naphthalenyl]carbonyl]-N-methylglycine, Methyl Ester 1-Hydroxybenzotriazole (1.63 g, 1.5 eq) and 1-(3-dimethylaminopropyl)-3-ethylcarbodiimide hydrochloride (185 g, 1.2 eq) were added sequentially to a stirred, room temperature solution of 2-ethoxy-6-methoxy-5-(trifluoromethyl)naphthoic acid (2.53 g, 8.05 mmol) in dry DMF (50 mL) under a dry N$_2$ atmosphere. After 1.5 hours, sarcosine methyl ester hydrochloride (2.25 g, 2 eq) and dry triethylamine (3.7 mL, 3.3 eq) were added. After 19 hours the reaction mixture was added to water (600 mL) and extracted with ether (3×300 mL). The aqueous phase was saturated with NaCl and extracted with ethyl acetate (2×200 mL). The combined organic extracts were washed with brine (500 mL). Silica gel (25 mL) was added to the organic extracts and the solvent was removed. The silica absorbate was flash chromatographed (1:1 petroleum ether:ethyl acetate) to provide an oil (3.12 g, 80%). The oil was triturated with petroleum ether to provide the product as an off white solid (2.59 g), m.p. 104°–105.5° C.

NMR (CDCl$_3$, 200 MHz, mixture of rotamers): δ1.30 (t, 3H, OCH$_2$CH$_3$), 2.77, 3.20 (2s, 3H, NCH$_3$), 3.43, 3.74 (2s, 3H, CO$_2$CH$_3$), 3.79 (d, 1H, —NCH$^1$H$^2$CO$_2$—), 3.86 (s, 3H, OCH$_3$), 4.11 (q, 2H, OCH$_2$CH$_3$), 4.88 (d, 1H, —N—CH$^1$H$^2$CO$_2$—), 7.22 (m, 2H, ArH), 8.03 (d, 1H, C8ArH), 8.12 (dm, 1H, ArH).

IR (CHCl$_3$, cm$^{-1}$): 1745 (CO$_2$CH$_3$), 1635 (CON);

Anal. Calcd.: C, 57.14; H, 5.05; N, 3.51%. Found: C, 57.28; H, 4.80; N, 3.48%.

Step (3) Preparation of N-[[2-Ethoxy-6-methoxy-5-(trifluoromethyl)-1-naphthalenyl]carbonyl]-N-methylglycine Aqueous sodium hydroxide (2.5N, 3.2 mL, 1.2 eq) was added to a room temperature, stirred solution of N-[[2-ethoxy-6-methoxy-5-(trifluoromethyl)-1-naphthalenyl]carbonyl]-N-methylglycine, methyl ester (2.64 g, 6.61 mmol) in THF (26 mL) and methanol (7 mL). After 1.5 hours, the solvents were removed. The residue was dissolved in water (100 mL) and extracted with ether (2×50 mL). These ether extracts were discarded. The aqueous phase was then acidified to pH 1 with concentrated HCl. The resulting oil-water mixture was extracted with ethyl acetate (100 mL). The ethyl acetate was concentrated and the resulting semisolid was triturated with petroleum ether to give a white solid product (2.56 g, 55%). The solid was recrystallized from ethanol-water to provide the title compound (1.40 g), m.p. 168°–170° C.

NMR (DMSO-d$^6$, 400 MHz): δ1.30 (t, 3H, J=7.0 Hz, OCH$_2$CH$_3$), 2.75 (s, 3H, NCH$_3$), 3.98 (s, 3H, OCH$_3$), 3.99 (d, 1H, J=17.2 Hz, NCH$^1$H$^2$CO$_2$—), 4.22 (q, 2H, J=7.0 Hz, (OCH$_2$CH$_3$), 4.56 (d, 1H, J=17.2 Hz, NCH$^1$H$^2$CO$_2$), 7.61 (m, 2H, ArH), 8.09 (m, 2H, ArH);

IR (KBr, cm$^{-1}$): 3650–2300 (CO$_2$H), 1745 (CO$_2$H), 1600 (CON);

MS (z/e): 385 (30%), 277 (97%), 269 (100%);

Anal. Calcd.: C, 56.11; H, 4.71; N, 3.63%. Found: C, 56.28; H, 4.55; N, 3.56%.

EXAMPLE 7

N-[[6-Methoxy-2-propoxy-5-(trifluoromethyl)-1-naphthalenyl]carbonyl]-N-methylglycine (I): R=—O—CH$_2$CH$_2$—CH$_3$; X==O; Y=—OH Step (1) Preparation of 6-Methoxy-2-propoxy-5-(trifluoromethyl)-1-naphthoic Acid Propanol (41.5 mL, 19.3 eq) was added to a stirred suspension of sodium hydride (18.0 g, 50% by weight dispersion in mineral oil, 13.1 eq) in dry THF (144 mL) with cooling in an ice bath, under a dry nitrogen atmosphere over a period of 12 minutes. After the gas evolution ceased, the ice bath was removed and copper (I) iodide (32.68 g, 6 eq) was added in two portions. A solution of 2-bromo-6-methoxy-5-trifluoromethyl-1-naphthoic acid, prepared by the process of Example 14, Step 2 (10.0 g, 0.0286 mole) in dry THF (50 mL) was then added. The reaction was heated to reflux for 1½ hours. The reaction mixture was allowed to cool, diluted with water (2 L) and acidified to pH 1 with concentrated hydrochloric acid. After stirring for 10 minutes, the mixture was filtered through celite. The celite was washed repeatedly with ethyl acetate (total 3 L). The water layer was extracted with ethyl acetate. The combined ethyl acetate phase was dried over magnesium sulfate and concentrated to give the product which was triturated with petroleum ether to give a brown solid (8.98 g, 95%). A small sample was further purified by recrystallization from ethanol water, m.g. 152°–154° C.

NMR (d$^6$DMSO, 200 MHz): δ1.05 (m, 3H, OCH$_2$CH$_2$CH$_3$), 1.90 (sextet, 2H, J=8 Hz, OCH$_2$CH$_2$CH$_3$), 3.98 (s, 3H, OCH$_3$), 4.22 (t, 2H, J=8 Hz, OCH$_2$CH$_2$CH$_3$), 7.37 (m, 2H, ArH), 8.33 (d, 1H, J=10 Hz, ArH), 8.80 (d, 1H, J=10 Hz, ArH);

IR (CHCl$_3$, cm$^{-1}$): 1710 (C=O);

Exact Mass. Calcd.: 328.0923; Found: 328.905.

Step (2) Preparation of N-[[6-Methoxy-2-propoxy-5-(trifluoromethyl)-1-naphthalenyl]carbonyl]-N-methylglycine, Methyl Ester 1-Hydroxybenzotriazole (5.42 g, 1.5 eq) and 1-(3-dimethylaminopropyl)-3-ethylcarbodiimide hydrochloride (6.14 g, 1.2 eq) were added to a mechanically stirred solution of 6-Methoxy-2-propoxy-5-(trifluoromethyl)-1-naphthoic acid (8.78 g, 0.0267 mol) in dry DMF (50 mL) at room temperature under a dry nitrogen atmosphere. After 1¾ hours sarcosine methyl ester hydrochloride (7.45 g, 2 eq) and triethylamine (12.6 mL) were added. After stirring 3½ hours at room temperature, the reaction mixture was diluted with water (2¼ L) and the organics were extracted with ether (4×700 mL). The extracts were combined, washed with saturated aqueous sodium chloride solution, dried over magnesium sulfate, absorbed onto silica gel and concentrated. The absorbate was flash chromatographed (60/40 petroleum ether/ethyl acetate) to give the product as a white solid (9.0 g, 81.5%), m.p. 74°–79° C.

NMR (CDCl$_3$, 200 MHz): δ1.00 (m, 3H, OCH$_2$CH$_2$CH$_3$), 1.80 (m, 2H, OCH$_2$CH$_2$CH$_3$), 2.84 (s, 3H, NCH$_3$), 3.83 (d, 1H, J=17 Hz, NCH$^1$H$^2$), 3.82 (s, 3H, COOCH$_3$), 3.95 (s, 3H, ArOCH$_3$), 4.00–4.11 (m, 2H, OCH$_2$CH$_2$CH$_3$), 4.98 (d, 1H, J=17 Hz, NCH$^1$H$^2$), 7.26–7.38 (m, 2H, ArH), 7.88–8.22 (m, 2H, ArH);

IR (CHCl$_3$, cm$^{-1}$): 1740 (C=O), 1630 (CON);

Anal. Calcd.: C, 58.11; H, 5.36; N, 3.39%. Found: C, 58.17; H, 5.64; N, 3.39%.

Step (3) Preparation of N-[[6-Methoxy-2-propoxy-5-(trifluoromethyl)-1-naphthalenyl]carbonyl]-N-methylglycine Sodium hydroxide (2.5N, 4.10 mL, 1.2 eq) was added to a stirred solution of N-[[6-methoxy-2-propoxy-5-(trifluoromethyl)-1-naphthalenyl]carbonyl]-N-methylglycine, methyl ester (3.50 g, 8.47 mmole) in THF (34 mL) and methanol (9 mL) at room temperature. After stirring 1¾ hours the solvents were removed. The residue was dissolved in water (250 mL). The aqueous phase was extracted with ether (2×100 mL). The extracts were discarded. The aqueous layer was acidified to pH 1 with 10% hydrochloric acid and then extracted with ethyl acetate (2×110 mL). The extracts were combined, dried over MgSO$_4$, concentrated and the residue was triturated with petroleum ether to give the product as a white solid (2.33 g, 69%), m.p. 70°–73° C.

NMR (CDCl$_3$, 400 MHz): δ1.03 (t, 3H, J=7 Hz, OCH$_2$CH$_2$CH$_3$), 1.83 (m, 2H, OCH$_2$CH$_2$CH$_3$), 2.89 (s, 3H, NCH$_3$), 3.96 (s, 3H, OCH$_3$), 4.02 (d, 1H, J=17 Hz, NCH$^1$H$^2$), 4.11 (t, 2H, J=6 Hz, OCH$_2$CH$_2$CH$_3$), 4.90

(d, 1H, J=17 Hz, NCH$^1$H$^2$), 7.29–7.36 (m, 2H, ArH), 8.03–8.26 (m, 2H, ArH);

IR (KBr, cm$^{-1}$): 1745 (C=O), 1605 (CON);

MS (z/e): 399 (14%), 311 (28%), 269 (100%), 268 (97%), 197 (22%), 182 (20%), 170 (26%), 169 (41%);

Anal. Calcd.: C, 57.14; H, 5.05; N, 3.51%. Found: C, 57.37; H, 4.85; N, 3.46%.

EXAMPLE 8

N-[[6-Methoxy-2-phenoxy-5-(trifluoromethyl)-1-naphthalenyl]carbonyl]-N-methylglycine (I):

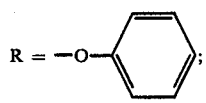

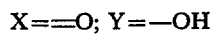

X==O; Y=—OH

Step (1) Preparation of 6-Methoxy-2-phenoxy-5-(trifluoromethyl)naphthoic Acid

Sodium hydride (9.83 g, 6.5 eq, 50% by weight dispersion in mineral oil) was added portionwise to a stirred solution of phenol (17.79 g, 6 eq) in dry THF (165 mL) cooled in an ice bath. After the gas evolution ceased copper (I) iodide (11.38 g, 3 eq) and 2-bromo-6-methoxy-5-trifluoromethyl-1-naphthoic acid, prepared by the process of Example 14, Step 2 (11.00 g, 31.5 mmol) were added. The ice bath was removed and the reaction mixture was heated to reflux for 45 minutes. The reaction mixture was cooled to room temperature, poured into water (2¼ L), diluted with ether (1 L) and filtered through celite. The filtrate was extracted with ethyl acetate (2×600 mL) and the celite was washed well with ethyl acetate (3 L). Extracts and washings were combined, dried over sodium sulfate, and concentrated to give a tan solid. After triturating with petroleum ether the solid was suspended in water (500 mL) and acidified to pH 1 with 10% HCl and extracted with ether (2×500 mL). The extracts were combined, washed with saturated sodium chloride solution, dried over magnesium sulfate and concentrated to give the crude product as a white solid (10.21 g, 89%). A small portion was purified by recrystallization from ethanol/water, m.p. 176°–178° C.

NMR (DMSO-d$^6$, 200 MHz): δ4.01 (s, 3H, OCH$_3$), 6.78–7.42 (m, 6H, ArH, PhH), 7.75 (d, 1H, J=10 Hz, ArH), 8.13 (dd, 2H, J=9.5 Hz, ArH);

IR (KBr, cm$^{-1}$): 3300–2700 (COOH), 1690 (C=O);

Anal. Calcd.: C, 62.99; H, 3.62%. Found: C, 63.01; H, 3.77%.

Step (2) Preparation of N-[[6-Methoxy-2-phenoxy-5-(trifluoromethyl)-1-naphthalenyl]carbonyl]-N-methylglycine, Methyl Ester 1-Hydroxybenzotriazole hydrate (5.71 g, 1.5 eq) and 1-(3-dimethylaminopropyl)-3-ethylcarbodiimide hydrochloride (6.49 g, 1.2 eq) were added to a stirred solution of 6-methoxy-2-phenoxy-5-(trifluoromethyl)naphthoic acid (10.2 g, 0.0282 mol) in dry DMF (182 mL) at room temperature under a dry nitrogen atmosphere. After stirring 1¾ hours at room temperature methyl sarcosinate hydrochloride (7.87 g, 2 eq) and triethylamine (13.3 mL) were added. After 4 hours the reaction mixture was diluted with water (2½ L) and extracted with ether (4×700 mL). Silica gel was added to the ether, the ether was removed and the absorbate was flash chromatographed (60/40 petroleum ether/EtOAc) to give the solid product (11.6 g, 92%), m.p. 125°–126° C.

NMR (DMSO-d$^6$, 200 Hz): δ2.85 (s, 3H, N—CH$_3$), 3.74 (s, 3H, COOCH$_3$), 4.02 (s, 3H, ArOCH$_3$), 4.09 (d, 1H, J=17 Hz, NCH$^1$H$^2$), 4.64 (d, 1H, J=17 Hz, NCH$^1$H$^2$), 7.03–7.42 (m, 6H, ArH, PhH), 7.78 (d, 1H, J=10 Hz, ArH), 8.12 (d, 1H, J=9 Hz, ArH), 8.22 (d, 1H, J=9 Hz, ArH);

IR (CHCl$_3$, cm$^{-1}$): 1740 (C=O), 1635 (CON);

Anal. Calcd.: C, 61.74; H, 4.50; N, 3.13%. Found: C, 61.60; H, 4.51; N, 3.29%.

Step (3) Preparation of N-[[6-Methoxy-2-phenoxy-5-(trifluoromethyl)-1-naphthalenyl]carbonyl]-N-methylglycine Aqueous sodium hydroxide (2.5N, 4.29 mL, 1.2 eq) was added to a stirred solution of N-[[6-methoxy-2-phenoxy-5-(trifluoromethyl)-1-naphthalenyl]carbonyl]-N-methylglycine, methyl ester (4.00 g, 8.94 mmol) in THF (34 mL) and methanol (9 mL). After 1 hour the solvents were removed and the residue was dissolved in water (250 mL). The aqueous phase was acidified to pH 1 with 10% HCl and a white solid precipitated. The solid was collected by filtration and purified by recrystallization from ethanol/water to give a white crystalline solid product (2.44 g, 63%), m.p. 180°–182° C.

NMR (DMSO-d$^6$, 400 MHz): δ2.83 (s, 3H, N—CH$_3$), 3.92 (d, 1H, J=17 Hz, NH$^1$H$^2$COOH), 4.02 (s, 3H, OCH$_3$), 4.57 (d, 1H, J=17 Hz, NH$^1$H$^2$COOH), 7.03–7.41 (m, 6H, ArH, PhH), 7.71 (d, 1H, J=9 Hz, ArH), 8.11 (d, 1H, J=9 Hz, ArH), 8.26 (d, 1H, J=9 Hz, ArH);

IR (KBr, cm$^{-1}$): 1760 (C=O), 1620 (CON);

MS (z/e): 433 (22%), 345 (100%), 302 (30%), 276 (23%), 233 (33%), 205 (22%), 169 (22%), 77 (52%);

Anal. Calcd.: C, 60.97; H, 4.19; N, 3.23%. Found: C, 61.14; H, 4.36; N, 3.21%.

EXAMPLE 9

N-[[2-Bromo-6-methoxy-5-(trifluoromethyl)-1-naphthalenyl]carbonyl]-N-methylglycine (I): R=—Br; X==O; Y=—OH Step (1) Preparation of N-[[2-Bromo-6-methoxy-5-(trifluoromethyl)-1-naphthalenyl]carbonyl]-N-methylglycine, Methyl Ester 1-(3-Dimethylaminopropyl)-3-ethylcarbodiimide (7.91 g, 1.2 eq) was added to a stirred solution of 2-bromo-6-methoxy-5-trifluoromethyl-1-naphthoic acid, prepared by the process of Example 14, Step 2 (12.00 g, 34.4 mmol) and 1-hydroxybenzotriazole (6.97 g, 1.5 eq) in anhydrous DMF (105 mL) at room temperature under a dry nitrogen atmosphere. Dissolution occurred after 20 minutes. After 1 hour, a suspension of methyl sarcosinate hydrochloride (9.56 g, 2.0 eq) in anhydrous DMF (60 mL) was added to the reaction mixture followed by triethylamine (15.8 mL, 3.3 eq). After 2¼ hours, more triethylamine (4.8 mL, 1.0 eq) was added. The reaction was diluted with water (1.6 L) after 18½ hours. The aqueous phase was extracted with ether (4×250 mL). The extracts were combined and washed with 0.5N sodium hydroxide solution (1×200 mL) and saturated aqueous sodium chloride (1×200 mL). The ether phase was dried with magnesium sulfate and the ether was removed. The crude product was flash chromatographed (3:2 to 2:3 petroleum ether:ethyl acetate eluent gradient, silica) then reflash chromatographed (99:1 to 9:1 methylene chloride:acetonitrile eluent gradient, silica) to provide the product as a white foam (11.16 g, 75%).

NMR (CDCl$_3$, 200 MHz) δ product is a 6:1 ratio of rotamers. Major rotamer reported first: 2.84, 3.28 (2s, 3H, NCH$_3$), 3.84 3.55 (2s, 3H, CO$_2$CH$_3$), 3.83 (d, 1H, J=17.1 Hz, NCH$^1$H$^2$CO$_2$), 3.99 (s, 3H, ArOCH$_3$), 5.03 (d, 1H, J=17.5 Hz, NCH$^1$H$^2$CO$_2$), 7.43, 7.34 (2d, 1H, J=9.5 Hz, ArH), 7.64, 7.62 (2d, 1H, J=8.6 Hz, ArH), 8.09, 8.00 (2d, 1H, J=8.6 Hz, ArH), 8.25 (d, 1H, J=9.6 Hz, ArH);

IR (CHCl$_3$, cm$^{-1}$): 1746 (C=O), 1642 (C=O), 1588 (C=C);

Exact Mass. Calcd.: 433.0137; Found: 433.0156.

Anal. Calcd.: C, 47.02; H, 3.48; N, 3.22%. Found: C, 45.65; H, 3.48; N, 3.13%.

Step (2) Preparation of N-[[2-Bromo-6-methoxy-5-(trifluoromethyl)-1-naphthalenyl]carbonyl]-N-methylglycine Methanol (12.5 mL) and aqueous sodium hydroxide (2.5N, 5.07 mL, 1.1 eq) were added to a stirred solution of N-[[2-bromo-6-methoxy-5-trifluoromethyl)-1-naphthalenyl]carbonyl]-N-methylglycine, methyl ester (5.00 g, 11.5 mmol) in THF (25 mL) at room temperature. After 40 minutes, the organic solvents were removed and the residue was dissolved in saturated aqueous sodium bicarbonate (75 mL). The basic phase was extracted with ether (1×30 mL), and the extract was discarded. The basic phase was diluted with water (100 mL) and acidified to pH 1 with concentrated hydrochloric acid. The acid phase was extracted with ethyl acetate (3×50 mL). The extracts were combined, dried with magnesium sulfate and the ethyl acetate was removed. The crude product was recrystallized in 1:1 chloroform:hexane to provide the product as white flakes (2.32 g, 48%), m.p. 163.5°–165° C.

NMR (d$^6$DMSO, 400 MHz): δ2.76 (s, 3H, NCH$_3$), 4.03 (d, 1H, J=17.2 Hz, NCH$^1$H$^2$CO$_2$), 4.03 (s, 3H, ArOCH$_3$), 4.61 (d, 1H, J=17.2 Hz, NCH$^1$H$^2$CO$_2$), 7.74 (d, 1H, J=9.6 Hz, ArH), 7.86 (d, 1H, J=9.4 Hz, ArH), 8.02 (d, 1H, J=7.75 Hz, ArH), 8.27 (d, 1H, J=9.6 Hz, ArH);

IR (KBr, cm$^{-1}$): 3440 (CO$_2$H), 1756 (C=O), 1621 (C=O);

Anal. Calcd.: C, 45.73; H, 3.12; N, 3.33%. Found: C, 45.42; H, 3.42; N, 3.27%.

EXAMPLE 10

N-[[2-Chloro-6-methoxy-5-(trifluoromethyl)-1-naphthalenyl]thioxomethyl]-N-methylglycine (I): R=—Cl; X==S; Y=—OH Step (1) Preparation of N-[[2-Chloro-6-methoxy-5-(trifluoromethyl)-1-naphthalenyl]thioxomethyl]-N-methylglycine, Methyl Ester Lawesson's reagent (1.9 g, 0.6 eq) was added to a stirred suspension of N-[[2-chloro-6-methoxy-5-(trifluoromethyl)-1-naphthalenyl]carbonyl]-N-methylglycine, methyl ester (3.00 g, 7.70 mmole) in toluene (30 mL) at room temperature under nitrogen. The reaction was heated to reflux for 42 hours with more Lawesson's reagent (3.9 g, 1.2 eq) added in three equal portions after 1¼, 17½ and 23½ hours. The reaction mixture was cooled to room temperature, filtered, and the filtrate absorbed onto silica gel and flash chromatographed (gradient elution:eluant 60/40, chloroform/petroleum ether →9/1 chloroform/acetonitrile) to provide the desired product as a foamy solid (0.98 g) and recovered starting material (1.23 g). The starting material (1.23 g, 3.08 mmole) was suspended in toluene (∼15 mL) and treated with Lawesson's reagent as described above to give additional product (0.351 g, combined yield 43%), m.p. 67°–73° C. (softens at 50° C.).

NMR (CDCl$_3$, 200 MHz): δ3.07 (s, 3H, —N—CH$_3$), 3.88 (s, 3H, COOCH$_3$), 3.98 (s, 3H, OCH$_3$), 4.27 (d, 1H, J=17 Hz, NCH$^1$H$^2$), 5.63 (d, 1H, J=17 Hz, NCH$^1$H$^2$), 7.43 (d, 1H, J=9 Hz, ArH), 7.48 (d, 1H, J=9 Hz, ArH), 8.10 (m, 1H, ArH), 8.21 (d, 1H, J=9 Hz, ArH);

IR (CHCl$_3$, cm$^{-1}$): 1745 (CO$_2$CH$_3$), 1612 (CON);

Anal. Calcd.: C, 49.70; H, 4.91; N, 3.41%. Found: C, 49.96; H, 4.66; N, 3.05%.

Step (2) Preparation of N-[[2-Chloro-6-methoxy-5-(trifluoromethyl)-1-naphthalenyl]thioxomethyl]-N-methylglycine Sodium hydroxide (2.5N, 1.4 mL, 1.2 eq) was added to a stirred solution of N-[[2-chloro-6-methoxy-5-trifluoromethyl)-1-naphthalenyl]thioxomethyl]-N-methylglycine, methyl ester (1.167 g, 2.88 mmol) in THF (11 mL) and methanol (3 mL) at room temperature. After 3 hours the organic solvents were removed. The residue was slurried in water (150 mL) and extracted with ether (3×50 mL). The extracts were discarded. The aqueous mixture was acidified to pH 1 with 10% hydrochloric acid and then extracted with ethyl acetate (2×50 mL). The extracts were combined, dried over magnesium sulfate, filtered and the ethyl acetate was removed. The resulting oil was triturated with hexane to give a cream colored solid product (0.76 g, 67%), m.p. 164°–166° C. (dec.).

NMR (d$^6$DMSO, 400 MHz): δ3.01 (s, 3N, NCH$_3$), 4.02 (s, 3H, —OCH$_3$), 4.62 (d, 1H, J=16 Hz, NCH$^1$H$^2$), 5.23 (d, 1H, J=16 Hz, NCH$^1$H$^2$) 7.72 (d, 2H, J=9 Hz, ArH), 8.03 (m, 1H, ArH), 8.25 (d, 1H, J=9 Hz, ArH);

IR (KBr, cm$^{-1}$): 3600–2500 (CO$_2$H), 1725 (CO$_2$H);

MS (z/e): 391 (50%), 356 (44%), 305 (36%), 303 (90%), 300 (29%), 262 (39%), 260 (100%), 241 (53%);

Anal. Calcd.: C, 49.05; H, 3.34; N, 3.57%. Found: C, 49.22; H, 3.56; N, 3.63%.

EXAMPLE 11

N-[[6-Methoxy-2-phenoxy-5-(trifluoromethyl)-1-naphthalenyl]thioxomethyl]-N-methylglycine Step (1) Preparation of N-[[6-Methoxy-2-phenoxy-5-(trifluoromethyl)-1-naphthalenyl]thioxomethyl]-N-methylglycine, Methyl Ester Lawesson's reagent (4.0 g, 0.6 eq) was added to a stirred suspension of N-[[6-methoxy-2-phenoxy-5-(trifluoromethyl)-1-naphthalenyl]carbonyl]-N-methylglycine, methyl ester prepared by the process of Example 8, Step 2 (7.4 g, 16 mmol) in dry toluene (74 mL) at room temperature under a nitrogen atmosphere. The reaction was heated to reflux for 22 hours with more Lawesson's reagent (4.0 g, 0.6 eq) added after 3 hours and (3.0 g, 0.5 eq) added after 6 hours. The reaction mixture was cooled to room temperature, absorbed onto silica gel and flash chromatographed (eluant methylene chloride) to give a pale yellow solid product (4.00 g, 52%). A small sample was purified by a second flash chromatograph (eluant 70/30 petroleum ether/ethyl acetate), to give a white solid, m.p. 133°–135° C.

NMR (CDCl$_3$, 200 MHz): δ3.19 (s, 3H, NCH$_3$), 3.86 (s, 3H, COOCH$_3$), 4.00 (s, 3H, OCH$_3$), 4.21 (d, 1H, J=17 Hz, NCH$^1$H$^2$), 5.70 (d, 1H, J=17 Hz, NCH$^1$H$^2$), 7.06–7.37 (m, 6H, ArH, PhH), 8.13 (d, 1H, J=12 Hz, ArH), 8.30 (d, 1H, J=10 Hz, ArH);

IR (KBr, cm$^{-1}$): 1748 (C=O);

MS (z/e): 463 (54%), 401 (20%), 361 (10%), 299 (40%), 71 (100%);

Exact Mass. Calcd.: 463.1066; Found: 463.1066.

Step (2) Preparation of N-[[6-Methoxy-2-phenoxy-5-(trifluoromethyl)-1-naphthalenyl]thioxomethyl]-N-methylglycine Sodium hydroxide (2.5N, 3.75 mL, 1.2 eq) was added to a stirred solution of N-[[6-methoxy-2-phenoxy-5-(trifluoromethyl)-1-naphthalenyl]thioxomethyl]-N-methylglycine, methyl ester (3.62 g, 7.81 mmol) in THF (30 mL) and methanol (8 mL) at room temperature. After 1 hour the organic solvents were removed. The residue was dissolved in water (250 mL) and extracted with ether (600 mL). The aqueous phase was further diluted with water (500 mL) and acidified to pH 1 with 10% HCl, then extracted with ethyl acetate (500 mL). The ethyl acetate extracts were combined, dried over magnesium sulfate, and concentrated to give a yellow solid product which was purified by trituraton with petroleum ether and recrystallization from chloroform/hexane to give 1.66 g, 47%, m.p. 112°–132° C. (dec.).

NMR (DMSO-$d^6$, 400 MHz): δ mixture of rotamers. Major peak reported first: 310, 3.53 (s, 3H, NC$\underline{H}_3$), 4.01, 3.98 (s, 3H, OC$\underline{H}_3$), 4.52 (d, 1H, J=16 Hz), NC$\underline{H}^1H^2$), 5.28 (d, 1H, J=17 Hz, NCH$^1\underline{H}^2$), 7.02–7.42 (m, 6H, Ar$\underline{H}$, Ph$\underline{H}$), 7.69 (d, 1H, J=10 Hz, Ar$\underline{H}$), 8.04 (d, 1H, J=10 Hz, Ar$\underline{H}$), 8.27 (d, 1H, J=9 Hz, Ar$\underline{H}$);

IR (KBr, cm$^{-1}$): 3300–2800 (COOH), 1720 (C=O);

MS (z/e): 449 (3.2%), 450 (22%), 91 (21%), 88 (21%), 169 (29%), 77 (100%);

Anal. Calcd.: C, 58.79; H, 4.04; N, 3.12%. Found: C, 58.86; H, 4.13; N, 3.12%.

EXAMPLE 12

N-[[2-Butoxy-6-methoxy-5-(trifluoromethyl)-1-naphthalenyl]carbonyl]-N-methylglycine Step (1) Preparation of 2-Butoxy-6-methoxy-5-(trifluoromethyl)-1-naphthoic Acid 1-Butanol (20.3 mL, dried over sieves) was added to a stirred suspension of sodium hydride (7.24 g, 13.1 eq, 50% by weight dispersion in mineral oil) in dry THF (74 mL) over a period of 10 minutes. Copper (I) iodide (13.14 g, 6 eq) was added in four portions with cooling in an ice bath. After the gas evolution ceased a solution of 2-bromo-6-methoxy-5-trifluoromethyl-1-naphthoic acid, prepared by the process of Example 14, Step 2 (4.00 g, 0.115 mol) in dry THF (50 mL) was added. The reaction mixture was heated to reflux for 35 minutes, allowed to cool to room temperature and then poured into water (2 L). The water phase was acidified to pH 1 with concentrated HCl, stirred for 15 minutes and the solid was filtered through celite. The aqueous filtrate was discarded. The solid was extracted with ethyl acetate (2 L). The ethyl acetate extract was dried over magnesium sulfate and concentrated to give a solid. This solid was diluted with water, acidified to pH 1 with concentrated HCl and filtered through celite. The filter cake was triturated with ethyl acetate (2×200 mL). Concentration of the combined ethyl acetate washings gave the tan solid product (2.8 g, 58%). A small portion was recrystallized from ethanol/water to give the analytical sample, m.p. 147°–151° C.

NMR (CDCl$_3$, 200 MHz): δ0.98 (t, 3H, J=7 Hz, —C$\underline{H}_2$CH$_3$), 1.56 (sextet, 2H, J=8 Hz, CH$_2$C$\underline{H}_2$CH$_3$), 1.82 (quintet, 2H, J=8 Hz, C$\underline{H}_2$CH$_2$CH$_3$), 3.98 (s, 3H, OC$\underline{H}_3$), 4.26 (t, 2H, J=6 Hz, OC$\underline{H}_2$CH$_2$CH$_2$CH$_3$), 7.35 (d, 1H, J=5 Hz, Ar$\underline{H}$), 7.40 (d, 1H, J=5 Hz, Ar$\underline{H}$), 8.34 (d, 1H, J=10 Hz, Ar$\underline{H}$), 8.75 (d, 1H, J=10 Hz, Ar$\underline{H}$);

IR (CHCl$_3$, cm$^{-1}$): 3300–2800 (COOH), 1720 (C=O);

Anal. Calcd.: C, 59.65; H, 5.00%. Found: C, 59.85; H, 4.90%.

Step (2) Preparation of N-[[2-Butoxy-6-methoxy-5-(trifluoromethyl)-1-naphthalenyl]carbonyl]-N-methylglycine, Methyl Ester 1-Hydroxybenzotriazole (1.54 g, 1.5 eq) and 1-(3-dimethylaminopropyl)-3-ethylcarbodiimide hydrochloride (1.75 g, 1.2 eq) were added to a stirred solution of 2-butoxy-6-methoxy-5-(trifluoromethyl)-1-naphthoic acid (2.60 g, 7.60 mmol) in dry DMF (50 mL) at room temperature under a dry nitrogen atmosphere. After 1.5 hours sarcosine methyl ester hydrochloride (2.12 g, 2 eq) and dry triethylamine (3.6 mL, 3.2 eq) were added. After 20 hours the reaction mixture was diluted with water (2½ L) and extracted with ether (2 L) and ethyl acetate. The extracts were combined, dried over MgSO$_4$, and purified by flash chromatography (eluant 60/40 petroleum ether/EtOAc) to give the product as a white solid (2.35 g, 72%). A small sample was triturated with petroleum ether to give the analytically pure sample, m.p. 104°–105° C.

NMR (CDCl$_3$, 200 MHz): δ0.95 (t, 3H, J=7 Hz, (CH$_2$)$_3$C$\underline{H}_3$), 1.48 (m, 2H, J=7 Hz, CH$_2$C$\underline{H}_2$CH$_2$CH$_3$), 1.76 (quintet, 2H, J=6 Hz, C$\underline{H}_2$CH$_2$CH$_2$CH$_3$), 2.83 (s, 3H, NC$\underline{H}_3$), 3.82 (d, 1H, J=17 Hz, NC$\underline{H}^1$H$^2$), 3.82 (s, 3H, COOC$\underline{H}_3$), 3.95 (s, 3H, OC$\underline{H}_3$), 4.12 (t, 2H, J=6 Hz, OC$\underline{H}_2$CH$_2$CH$_2$CH$_3$), 4.99 (d, 1H, J=17 Hz, NCH$^1\underline{H}^2$), 7.26 (d, 1H, J=9 Hz, Ar$\underline{H}$), 7.36 (d, 1H, J=10 Hz, Ar$\underline{H}$), 8.10 (d, 1H, J=9 Hz, Ar$\underline{H}$), 8.21 (d, 1H, J=9 Hz, Ar$\underline{H}$);

IR (CHCl$_3$, cm$^{-1}$): 1745 (C=O), 1635 (CON), 1600 (C=C);

Anal. Calcd.: C, 59.01; H, 5.66; N, 3.28%. Found: C, 58.80; H, 5.85; N, 3.24%.

Step (3) Preparation of N-[[2-Butoxy-6-methoxy-5-(trifluoromethyl)-1-naphthalenyl]carbonyl]-N-methylglycine Aqueous sodium hydroxide (2.5N, 2.7 mL, 1.2 eq) was added to a stirred solution of N-[[2-butoxy-6-methoxy-5-(trifluoromethyl)-1-naphthalenyl]carbonyl]-N-methylglycine, methyl ester (2.35 g, 5.50 mmol) in THF (22 mL) and methanol (6 mL) at room temperature. After 1½ hours the organic solvents were removed and the residue was taken up in water (250 mL). The aqueous phase was acidified to pH 1 with 10% HCl, then extracted with ethyl acetate. The extracts were combined, dried over MgSO$_4$, and concentrated to give a solid which was triturated with petroleum ether to provide the title compound as a white solid (1.57 g, 69%), m.p. 152°–155° C.

NMR (DMSO-$d^6$, 400 MHz): δ mixture of rotamers. Major rotamer reported first: 0.91 (t, 3H, J=7 Hz, CH$_2$CH$_2$CH$_2$C$\underline{H}_3$), 1.41 (sextet, 2H, J=7 Hz, CH$_2$C$\underline{H}_2$CH$_2$CH$_3$), 1.67 (quintet, 2H, J=5 Hz, CH$_2$CH$_2$C$\underline{H}_2$CH$_3$), 2.73, 3.13 (s, 3H, NC$\underline{H}_3$), 3.97, 3.94 (s, 3H, OC$\underline{H}_3$), 3.97 (d, 1H, J=17 Hz, NC$\underline{H}^1$H$^2$), 4.14 (m, 2H, OC$\underline{H}_2$CH$_2$CH$_2$CH$_3$), 4.54 (d, 1H, J=17 Hz, NCH$^1\underline{H}^2$), 7.59 (m, 2H, Ar$\underline{H}$), 8.06–8.09 (m, 2H, Ar$\underline{H}$);

IR (KBr, cm$^{-1}$): 1750 (C=O), 1605 (C=O);

Anal. Calcd.: C, 58.11; H, 5.36; N, 3.38%. Found: C, 58.36; H, 5.40; N, 3.46%.

EXAMPLE 13

2-Fluoro-6-methoxy-5-(trifluoromethyl)-1-naphthoic Acid (II): $R^1 = -F$

Step (1) Preparation of 1-Bromomethyl-2-fluoro-6-methoxy-5-(trifluoromethyl)naphthalene A suspension of N-bromosuccinimide (6.93 g, 1.1 eq), benzoyl peroxide (38 mg) and 2-fluoro-6-methoxy-1-methyl-5-(trifluoromethyl)naphthalene (9.14 g, 35.39 mmol) in carbontetrachloride (160 mL) was heated to reflux with stirring under a dry nitrogen atmosphere for 1.5 hours. The reaction mixture was cooled to room temperature and filtered. The solid was washed with carbon tetrachloride (3×30 mL). The solvent was removed from the combined CCl$_4$ phases to provide the product as a white solid in quantitative yield. A small portion of this solid was recrystallized from hexane:ethylacetate, m.p. 97°–100° C.

NMR (CDCl$_3$, 200 MHz): δ4.01 (s, 3H, OCH$_3$), 4.94 (d, 2H, J=1.5 Hz, CH$_2$Br), 7.32 (t, 1H, J=9.4 Hz, ArH), 7.49 (d, 1H, J=9.5 Hz, ArH), 8.25 (m, 1H, ArH), 8.25 (d, 1H, ArH);

IR (CHCl$_3$, cm$^{-1}$): 1615 (aromatic C-C).

Anal. Calcd.: C, 46.32; H, 2.69%. Found: C, 46.04; H, 2.34%.

Step (2) Preparation of 2-Fluoro-1-hydroxymethyl-6-methoxy-5-(trifluoromethyl)naphthalene A suspension of 1-bromomethyl-2-fluoro-6-methoxy-5-(trifluoromethyl)naphthalene (11.16 g, 35 mmol), sodium formate (5.85 g, 86 mmol), ethanol (134 mL) and water (34 mL) was heated to reflux with stirring. Dissolution occurred within 20 minutes. After 1.5 hours the heating source was removed, 2.5N NaOH (14 mL) was added, and the reaction mixture was cooled to room temperature. The ethanol was removed, water (100 mL) was added and the solid was filtered. The white solid was washed with water and dried in vacuo to give the product in quantitative yield. A small portion was recrystallized from petroleum ether:ethyl acetate, m.p. 113°–114° C.

NMR (CDCl$_3$, 200 MHz): δ1.74 (t, 1H, J=6.2 Hz, —OH), 3.99 (s, 3H, OCH$_3$), 5.15 (dd, 2H, J=1.3 and 6.2 Hz, —CH$_2$OH), 7.32 (t, 1H, J=9.4 Hz, ArH), 7.42 (d, 1H, J=9.4 Hz, ArH), 8.18 (m, 1H, ArH), 8.41 (d, 1H, J=9.4 Hz, ArH);

IR (CHCl$_3$, cm$^{-1}$): 3610, 3420 (OH), 1615 (aromatic C-C);

Anal. Calcd.: C, 56.94; H, 3.67%. Found: C, 56.71; H, 3.86%.

Step (3) Preparation of 2-Fluoro-6-methoxy-5-(trifluoromethyl)-1-naphthoic Acid

Jones reagent (2.67M in CrO$_3$, 25 mL, 66.8 mmol) was added dropwise over a 5 minute period to a mechanically stirred, cold (0°–10° C.) solution of 2-fluoro-1-hydroxymethyl-6-methoxy-5-(trifluoromethyl)naphthalene (11.59 g, 34.6 mmol) in acetone (120 mL). The reaction mixture was warmed to room temperature and after 2 hours it was quenched with isopropanol. The reaction mixture was diluted with ether to a volume of ~500 mL and then filtered through celite. The celite was washed with more ether. The ether was removed and the residue was dissolved in 5% NaOH (100 mL). An additional 100 mL of water was added and this aqueous phase was extracted with ether (4×200 mL), ethyl acetate (1×100 mL) and CH$_2$Cl$_2$ (1×200 mL). These extracts were discarded. The base phase was acidified to pH 1–3 with 10% HCl and the tan solid was collected and dried in vacuo (7.3 g, 73%). A small sample was recrystallized from ethanol:water, m.p. 179°–181° C.

NMR (CDCl$_3$, 200 MHz): δ4.02 (s, 3H, OCH$_3$), 7.40 (t, 1H, J=9.5 Hz, ArH), 7.46 (d, 1H, J=9.6 Hz, ArH), 8.37 (m, 1H, ArH), 8.53 (d, 1H, J=9.6 Hz, ArH);

IR (KBr, cm$^{-1}$): 3600–2500 (CO$_2$H), 1695 (CO$_2$H).

Exact Mass.: Calcd.=288.0409; Found=288.0380.

EXAMPLE 14

6-Methoxy-2-(2,2,2-trifluoroethoxy)-5-(trifluoromethyl)naphthoic Acid (II): $R^1 = -O-CH_2-CF_3$ Step (1) Preparation of (2-Bromo-6-methoxy-5-trifluoromethyl-1-naphthalenyl)methanol According to the procedure of E. L. Eliel et al, J. Chem. Soc., 1628 (1955), sodium formate (12.88 g, 2.4 eq) and water (42 mL) were added to a stirred suspension of 2-bromo-1-bromomethyl-6-methoxy-5-trifluoromethylnaphthalene (32.4 g, 78.0 mmol, prepared by the process of Example 13) in ethanol (160 mL) at room temperature. The suspension was heated to reflux and after 1 hour, more sodium formate (1.07 g, 0.2 eq) was added. After 10¾ hours, water (25 mL) was added and the ethanol was removed by distillation. The reaction was cooled to room temperature and basified to pH 9 with 10% aqueous sodium hydroxide solution. The basic suspension was diluted with water (1.5 L) and filtered. The solid was washed with water (2×30 mL) then triturated with chloroform (2×25 mL) and dried to provide the light yellow solid (23.10 g, 87%). A small sample was flash chromatographed (7:3 to 3:2 petroleum ether:ethyl acetate eluant gradient, silica), to provide a white solid for analysis, m.p. 171°–173° C.

NMR (d$^6$DMSO, 200 MHz): δ4.01 (s, 3H, ArOCH$_3$), 5.07 (d, 2H, J=4.4 Hz, CH$_2$OH), 5.44 (t, 1H, J=5.2 Hz, CH$_2$OH), 7.70 (d, 1H, J=9.5 Hz, ArH), 7.78 (d, 1H, J=9.1 Hz, ArH), 7.90 (d, 1H, J=9.9 Hz, ArH), 8.56 (d, 1H, J=10.2 Hz, ArH);

IR (KBr, cm$^{-1}$): 3318 (OH), 1613 and 1588 (C=C);

Anal. Calcd.: C, 46.59; H, 3.01%. Found: C, 46.77; H, 3.36%.

Step (2) Preparation of 2-Bromo-6-methoxy-5-trifluoromethyl-1-naphthoic Acid

Jones reagent (2.67M in CrO$_3$, 34 mL, 1.32 eq) was added slowly to a stirred solution of (2-bromo-6-methoxy-5-trifluoromethyl-1-naphthalenyl)methanol (23.10 g, 68.9 mmol) in acetone (450 mL) at 0° C. After 5 minutes, the reaction was warmed to room temperature. After 1 hour, more Jones reagent (6.8 mL, 0.26 eq) was added. After 2½ hours, the reaction was quenched with isopropanol (10 mL) and diluted with water (1.4 L). The aqueous phase was extracted with ethylacetate (3×400 mL). The extracts were combined; the ethyl acetate phase was quickly extracted with 5N sodium hydroxide solution (3×350 mL). The base extracts were combined and acidified to pH 1 with concentrated hydrochloric acid. The aqueous acid suspension was stirred overnight at room temperature. The solid was collected by suction filtration, washed with water (1×25 mL), and dried to provide the light yellow solid (16.05 g, 67%), m.p. 221°–222.5° C.

NMR (d$^6$DMSO, 400 MHz): δ4.02 (s, 3H, ArOCH$_3$), 7.77 (d, 1H, J=9.7 Hz, ArH), 7.84 (d, 1H, J=9.4 Hz, ArH), 8.02 (d, 2H, J=9.3 Hz, ArH);

IR (KBr, cm$^{-1}$): 1710 (C=O), 1612 and 1583 (C=C);

MS (z/e): 350 (99%), 348 (100%), 333 (20%), 331 (20%), 307 (24%), 305 (26%);

Anal. Calcd.: C, 44.73; H, 2.31%. Found: C, 44.69; H, 2.38%.

Step (3) Preparation of 6-Methoxy-2-(2,2,2-trifluoroethoxy)-5-(trifluoromethyl)naphthoic Acid 2,2,2-Trifluoroethanol (8.35 mL, 4.0 eq) was added slowly to a suspension of sodium hydride (60% by weight dispersion in mineral oil, 7.68 g, 6.7 eq) in anhydrous hexamethylphosphoramide (85 mL) at room temperature contained in a flame dried reaction vessel under argon. After 20 minutes, 2-bromo-6-methoxy-5-trifluoromethyl-1-naphthoic acid (10.00 g, 28.6 mmol) and copper (I) iodide (10.91 g, 2.0 eq) were added with care. After 50 minutes, the reaction was heated to 65° C. for 1½ hours, then cooled to room temperature. The reaction was diluted with water (800 mL) and acidified to pH1 with concentrated hydrochloric acid. The acid phase and ethyl acetate (200 mL) were stirred together for 15 minutes then filtered through celite; the celite was washed with more ethyl acetate (2×100 mL). The two layers of the filtrate were separated. The aqueous layer was extracted with ethyl acetate (2×150 mL). All the ethyl acetae phases were combined and the ethyl acetate was removed. The residue was dissolved in 0.5N sodium hydroxide (800 mL) and extracted with ether (2×150); the extracts were discarded. The base phase was acidified to pH1 with concentrated hydrochloric acid. The acid phase was extracted with ether (3×200 mL). The extracts were combined, washed with saturated aqueous sodium chloride (1×50 mL), dried with magnesium sulfate, and the ether was removed to provide the light yellow solid (9.33 g, 88%). A small sample was recrystallized in ethanol:water for analysis, m.p. 190°–192° C.

NMR (d$^6$DMSO, 200 MHz): δ3.99 (s, 3H, ArOCH$_3$), 4.93 (q, 2H, J=8.9 Hz, OCH$_2$CF$_3$), 7.71 (2d, 2H, J=4.4 and 9.4 Hz, ArH), 8.00 (d, 1H, J=9.5 Hz, ArH), 8.13 (d,1H, J=8.4 Hz, ArH);

IR (KBr, cm$^{-1}$): 1718 (C=O), 1614 (C=C);

Anal. Calcd.: C, 48.93; H, 2.74%. Found: C, 48.90; H, 3.13%.

EXAMPLE 15

Step (1) Preparation of 1-Bromomethyl-2-chloro-6-methoxy-5-trifluoromethylnaphthalene N-Bromosuccinimide (11.62 g, 1.1 eq) and benzoylperoxide (0.061 g, 0.0044 eq) were added to a stirred solution of 2-chloro-6-methoxy-1-methyl-5-trifluoromethylnaphthalene (16.3 g, 0.0593 mol, prepared by the process of Example 17, Step (2) in carbon tetrachloride (200 mL) at room temperature, under a dry nitrogen atmosphere. The reaction was heated to reflux for 29 hours with additional N-bromo-succinamide (10.55 g, 1 eq) and benzoylperoxide (0.035 g, 0.0025 eq) added after 5½ hours. The reaction mixture was cooled to room temperature and filtered. The solid was washed with hot carbon tetrachloride. The filtrate was concentrated to provide the white solid product (21.88 g, 100%). A small sample was purified by flash chromatography (4/1 petroleum ether/chloroform) to give analytical sample, m.p. 127°–130° C.

NMR (CDCl$_3$, 200 MHz): δ4.01 (s, 3H, OCH$_3$), 5.05 (s, 2H, CH$_2$Br), 7.46 (d, 1H, J=8 Hz, ArH), 7.50 (d, 1H, J=7 Hz, ArH), 8.13 (d, 1H, J=8 Hz, ArH), 8.26 (d, 1H, J=10 Hz, ArH);

IR (CHCl$_3$, cm$^{-1}$): 1610 and 1580 (C=C);

Anal. Calcd.: C, 44.16; H, 2.56%. Found: C, 44.13; H, 2.46%.

Step (2) Preparation of 2-Chloro-1-hydroxymethyl-6-methoxy-5-trifluoromethylnaphthalene Sodium formate (9.68 g, 2.4 eq) and water (57 mL) were added to a stirred suspension of 1-bromomethyl-2-chloro-6-methoxy-5-trifluoromethylnaphthalene (20.97 g, 0.0593 mol) in ethanol (226 mL) at room temperature. The reaction mixture was heated to reflux for 3½ hours. The heat was removed and 2.5N sodium hydroxide (27 mL, 1 eq) was added to the stirred hot mixture. The ethanol was removed and the residue was diluted with water (~100 mL). The aqueous suspension was filtered. The solid was washed with water and dried in vacuo to provide the off white solid product (16.01 g, 93%). A small sample was purified by flash chromatography (3/2 petroleum ether:ethyl acetate) to give an analytical sample, m.p. 162°–166° C.

NMR (CDCl$_3$, 200 MHz): δ1.86 (t, 1H, J=5 Hz, —CH$_2$OH), 4.04 (s, 3H, OCH$_3$), 5.29 (d, 2H, J=5 Hz, CH$_2$OH), 7.44 (d, 1H, J=10 Hz, ArH), 7.53 (d, 1H, J=10 Hz, ArH), 8.16 1H, J=10 Hz, ArH); (d, 1H, J=10 Hz, ArH), 8.46 (d, 1H, J=10 Hz, ArH);

IR (KBr, cm$^{-1}$): 3290 (—OH), 1608 (C=C);

Anal. Calcd.: C, 53.90; H, 3.13%. Found: C, 53.81; H, 3.36%.

Step (3) Preparation of 2-Chloro-6-methoxy-5-(trifluoromethyl)naphthoic Acid

Jones reagent (2.67M in CrO$_3$, 27 mL, 1.34 eq) was added to a mechanically stirred solution of 2-chloro-1-hydroxymethyl-6-methoxy-5-trifluoromethylnaphthalene (15.61 g, 0.0537 mol) in acetone (324 mL) at 0° C. The reaction mixture was warmed to room temperature and stirred for 4 hours with another 10 mL (0.50 eq) of Jones reagent added after 2 hours. The reaction was quenched with isopropanol (~250 mL), diluted with ether (~1 L), and filtered through celite. The filtrate was concentrated and the residue was dissolved in 5% NaOH (150 mL). The aqueous phase was extracted with ether (1 L) and methylene chloride (500 mL). The extracts were discarded. The aqueous phase was acidified to pH1 with 10% hydrochloric acid. The solid precipitate was filtered, washed with water and dried in vacuo at 80° C. to give the product as a white solid (10.98 g, 67%). A small portion was recrystallized from chloroform/petroleum ether to give the analytical sample, m.p. 214° C. (dec.).

NMR (d$^6$DMSO, 200 MHz): δ4.02 (s, 3H, OCH$_3$), 7.75 (t, 2H, J=10 Hz, ArH), 8.03 (d, 1H, J=10 Hz, ArH), 8.11 (d, 1H, J=10 Hz, ArH);

IR (KBr, cm$^{-1}$): 3600–2500 (CO$_2$H), 1687 (C=O);

Anal. Calcd.: C, 51.25; H, 2.65%. Found: C, 50.89; H, 2.84%.

EXAMPLE 16

Preparation of 2-Bromo-1-bromomethyl-6-methoxy-5-trifluoromethylnaphthalene

N-Bromosuccinimide (21.07 g, 1.5 eq) and benzoyl peroxide (84 mg, 0.0044 eq) were added to a stirred solution of 2-bromo-6-methoxy-1-methyl-5-trifluoromethylnaphthalene (25.19 g, 78.9 mmol, prepared by the process of Example 17, Step 1) in carbon tetrachloride (300 mL) at room temperature under a dry nitrogen atmosphere. The reaction was heated to reflux for 6 hours, then cooled to ~50° C. The warm reaction mixture was filtered. The solid was washed with warm carbon tetrachloride (2×30 mL). The carbon tetrachloride was removed from the filtrate to provide the light yellow solid (32.4 g, 100%), m.p. 141.5–143° C.

NMR (CDCl$_3$, 200 MHz): δ4.02 (s, 3H, OCH$_3$), 5.09 (s, 2H, CH$_2$Br), 7.46 (d, 1H, J=9.5 Hz, Ar$\underline{H}$), 7.66 (d, 1H, J=9.5 Hz, Ar$\underline{H}$), 8.06 (dm, 1H, Ar$\underline{H}$), 8.30 (d, 1H, J=9.5 Hz, Ar$\underline{H}$);

IR (CHCl$_3$, cm$^{-1}$): 1615, 1585 (ArC-C);

Anal. Calcd.: C, 39.23; H, 2.28%. Found: C, 38.90; H, 2.41%.

EXAMPLE 17

Step (1) Preparation of 2-Bromo-6-methoxy-1-methyl-5-trifluoromethylnaphthalene

A solution of bromine (6.41 mL, 0.125 mol) in glacial acetic acid (28 mL) was added to a stirred solution of 2-methoxy-5-methyl-1-trifluoromethylnaphthalene (20.9 g, 0.083 mmol) in glacial acetic acid (300 mL) over a 25 minute period. The solution was stirred at room temperature for 22 hours. The reaction mixture was poured into dilute aqueous NaHSO$_3$ (2 L). The yellow solid product was collected via suction filtration and dried in vacuo (26.2 g, 98%), m.p. 98°–100.5° C.

NMR (CDCl$_3$, 200 MHz): δ2.77 (s, 3H, CH$_3$), 3.99 (s, 3H, OCH$_3$), 7.33 (d, 1H, J=9.5 Hz, Ar$\underline{H}$), 7.63 (d, 1H, J=9.6 Hz, Ar$\underline{H}$), 7.91 (dm, 1H, Ar$\underline{H}$), 8.19 (d, 1H, J=9.5 Hz, Ar$\underline{H}$);

IR (CHCl$_3$, cm$^{-1}$): 1610 (ArC-C);

Anal. Calcd.: C, 48.93; H, 3.16%. Found: C, 48.57; H, 3.38%.

Step (2) Preparation of 2-Chloro-6-methoxy-1-methyl-5-trifluoromethylnaphthalene Copper (I) chloride (35.78 g, 6 eq) was added to a solution of 2-bromo-6-methoxy-1-methyl-5-trifluoromethylnaphthalene (19.22 g, 0.0602 mol) in dry DMSO (194 mL) at room temperature under a nitrogen atmosphere. The reaction mixture was heated at ~188° C. for 3 hours, then cooled to room temperature and diluted with water (3 L). The resultant solids were collected and triturated well with ethyl acetate (2 L total). The triturates were combined, dried over magnesium sulfate, filtered, and the solvent removed to give the desired product as a white solid (16.7 g, 100%). A small sample was purified by flash chromatography (eluant 90/10 petroleum ether/chloroform) to give an analytically pure product, m.p. 102°–103° C.

NMR (CDCl$_3$, 200 MHz): δ2.72 (s, 3H, —CH$_3$), 3.99 (s, 3H, OCH$_3$), 7.34 (d, 1H, J=10 Hz, Ar$\underline{H}$), 7.48 (d, 1H, J=10 Hz, Ar$\underline{H}$), 7.98 (d, 1H, J=9 Hz, Ar$\underline{H}$), 8.17 (d, 1H, J=10 Hz, Ar$\underline{H}$);

IR (CHCl$_3$, cm$^{-1}$): 2950 and 2858 (CH), 1610 and 1590 (C=C);

Anal. Calcd.: C, 56.85; H, 3.67%. Found: C, 56.57; H, 3.95%.

EXAMPLE 18

2-Fluoro-6-methoxy-1-methyl-5-(trifluoromethyl)naphthalene

Step (1) Preparation of
2-Methoxy-5-methyl-6-nitro-1-(trifluoromethyl)naphthalene To a cooled solution (3° to 4° C.) of acetic anhydride (640 mL) was added fuming nitric acid (90%, specific gravity=1.5, 160 mL) dropwise via an addition funnel at such a rate as to keep the internal temperature at or below 8° C. (~1 hour 20 minutes total addition time). After the internal temperature had again cooled to 3°–4° C., 2-methoxy-5-methyl-1-trifluoromethylnaphthalene (200 g, 0.833 mol) was added portion wise. The portions added were small enough such that the internal temperature did not rise above 10° C. and each portion was added when the temperature had cooled to 5° C. (addition time ~1 hour 15 minutes). After an additional 15 minutes the reaction mixture was added to water (3 L). The resulting amorphous solid was filtered, washed with water and the lumps broken up and dried in vacuo overnight. The dry solid (~225 g) was recrystallized from 95:5 ethanol:isopropanol (3 L). The resulting long yellow needles were filtered and washed with ethanol (2×50 mL) to provide the product (97.5 g, 41%), m.p. 141°–142° C. A small amount of the desired product was recrystallized from 4:1 petroleum ether:ethyl acetate.

NMR (CDCl$_3$, 200 MHz): δ2.84 (s, 3H, CH$_3$), 4.05 (s, 3H, OCH$_3$), 7.47 (d, 1H, J=10.0 Hz, Ar$\underline{H}$), 7.87 (d, 1H, J=9.9 Hz, Ar$\underline{H}$), 8.16 (dm, 1H, Ar$\underline{H}$), 8.39 (d, 1H, J=10.0 Hz, Ar$\underline{H}$);

IR (CHCl$_3$, cm$^{-1}$): 1615 (aromatic C=C);

MS (z/e): 285 (67%), 268 (80%), 266 (13%), 248 (48%), 240 (42%), 196 (100%), 146 (100%);

Anal. Calcd.: C, 60.47; H, 3.90%. Found: C, 60.28; H, 3.80%.

Step (2) Preparation of 6-Amino-2-methoxy-5-methyl-1-trifluoromethylnaphthalene

A suspension of 2-methoxy-5-methyl-6-nitro-1-trifluoromethylnaphalene (16.5 g, 57.85 mmol), 10% palladium on carbon (1.69 g) in absolute ethanol (900 mL) was hydrogenated at 40 psi H$_2$ pressure at room temperature for 2 hours. The reaction mixture was then filtered through sulkafloc and the sulkafloc was washed with fresh ethanol. The ethanol was then removed from the filtrate to provide the product as a yellow solid (14.3 g, 97%), m.p. 109°–110° C.

NMR (CDCl$_3$, 200 MHz): δ2.40 (s, 3H, CH$_3$), 3.77 (broad s, 2H, NH$_2$), 3.95 (s, 3H, OCH$_3$), 7.04 (d, 1H, J=9.7 Hz, Ar$\underline{H}$), 7.26 (d, 1H, J=9.5 Hz, Ar$\underline{H}$), 7.92 (dm, 1H, Ar$\underline{H}$), 8.05 (d, 1H, J=9.5 Hz, Ar$\underline{H}$);

IR (CHCl$_3$, cm$^{-1}$): 3510, 3420 (NH$_2$), 1630, 1610 (aromatic C-C);

MS (z/e): 255 (100%), 234 (79%), 212 (75%);

Anal. Calcd.: C, 61.17; H, 4.74; N, 5.49%. Found: C, 61.38; H, 4.40; N, 5.40%.

Step (3) Preparation of 2-Fluoro-6-methoxy-1-methyl-5-(trifluoromethyl)naphthalene A 250 mL nalgene bottle with magnetic stir bar under an N$_2$ atmosphere was charged with HF-pyridine (75 mL) and cooled to −78° C. in a dry ice-isopropanol bath. When the HF-pyridine solution was frozen, a solution of the 6-amino-2-methoxy-5-methyl-1-trifluoromethylnaphthalene (10.07 g, 39.4 mmol) in pyridine (25 mL, previously dried over KOH) was added slowly. Again, when the solution was frozen, solid sodium nitrite (4.55 g, 1.67 eq) was added and the dry ice-isopropanol bath was removed. The reaction mixture was stirred at room temperature for 30 minutes (after 10 minutes the frozen solids had melted). The reaction mixture was then heated in a 65° C. oil bath for 2 hours. During this heating period a foamy precipitate had collected in the reaction vessel. The reaction mixture was cooled to room temperature and added to water (1 L). The aqueous phase was extracted with ether (3×300 mL). The combined ether extracts were washed with saturated aqueous NaCl (200 mL). Silica gel (40 mL) was added to the ether phase and the ether was removed. The silica absorbate was flash chromatographed (95:5 petroleum ether:ethyl acetate) to provide the white solid product (7.82 g, 77%), m.p. 97°–99° C.

NMR (CDCl$_3$, 200 MHz): δ2.56 (d, 3H, J=2.2 Hz, C$\underline{H}_3$), 3.99 (s, 3H, OC$\underline{H}_3$), 7.28 (d, 1H, J=9.3 Hz, Ar$\underline{H}$), 7.34 (t, 1H, J=9.3 Hz, Ar$\underline{H}$), 8.04 (m, 1H, Ar$\underline{H}$), 8.13 (d, 1H, J=9.3 Hz, Ar$\underline{H}$);

IR (CHCl$_3$, cm$^{-1}$): 1615 (aromatic C-C);

MS (z/e): 258 (96%);

Anal. Calcd.: C, 60.47; H, 3.98%. Found: C, 60.28; H, 3.81%.

We claim:
1. The compound N-2-fluoro-6-methoxy-N-methyl-5-(trifluoromethyl)-1-naphthalenecarboxamide, or the pharmaceutically acceptable salt thereof.
2. The N-2-fluoro-6-methoxy-N-methyl-5-(trifluoromethyl)-1-naphthalenecarboxamide, or the pharmaceutically acceptable salt thereof.
3. The compound acetamide, or the pharmaceutically acceptable salt thereof.

* * * * *

UNITED STATES PATENT AND TRADEMARK OFFICE
CERTIFICATE OF CORRECTION

PATENT NO. : 4,962,224

DATED : October 9, 1990

INVENTOR(S) : Jay E. Wrobel, John G. Bauman and Kazimir Sestanj

It is certified that error appears in the above—identified patent and that said Letters Patent is hereby corrected as shown below:

At title page, right col. last line "2 Claims" should read ---3 Claims---.

At col. 40, line 1 to 10 amended claims 1, 2 and 3 should read:

1. The compound N-[(aminocarbonyl)methyl]-2-fluoro-6-methoxy-N-methyl-5-(trifluoromethyl)-1-naphthalenecarboxamide, or the pharmaceutically acceptable salt thereof.

2. The compound N-[2-[(ethoxycarbonyl)amino]-2-oxoethyl]-2-fluoro-6-methoxy-N-methyl-5-(trifluoromethyl)-1-naphthalenecarboxamide, or the pharmaceutically acceptable salt thereof.

3. The compound [[[2-fluoro-6-methoxy-5-(trifluoromethyl)-1-naphthalenyl]-thioxomethyl]methylamino]acetamide, or the pharmaceutically acceptable salt thereof.

Signed and Sealed this

Fourteenth Day of January, 1992

*Attest:*

HARRY F. MANBECK, JR.

*Attesting Officer*  *Commissioner of Patents and Trademarks*